United States Patent
Farmer et al.

(10) Patent No.: US 11,149,303 B2
(45) Date of Patent: *Oct. 19, 2021

(54) METHODS OF DEPLETING A TARGET NUCLEIC ACID IN A SAMPLE AND KITS FOR PRACTICING THE SAME

(71) Applicant: TAKARA BIO USA, INC., Mountain View, CA (US)

(72) Inventors: Andrew Alan Farmer, Los Altos, CA (US); Ian B. Oglesby, Mountain View, CA (US); Magnolia Bostick, San Mateo, CA (US); Steve Oh, Sunnyvale, CA (US)

(73) Assignee: Takara Bio USA, Inc., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/537,160

(22) Filed: Aug. 9, 2019

(65) Prior Publication Data

US 2019/0360032 A1 Nov. 28, 2019

Related U.S. Application Data

(60) Division of application No. 15/217,923, filed on Jul. 22, 2016, now Pat. No. 10,421,992, which is a continuation of application No. 14/023,354, filed on Sep. 10, 2013, now Pat. No. 9,428,794.

(60) Provisional application No. 61/700,727, filed on Sep. 13, 2012.

(51) Int. Cl.
*C12Q 1/68* (2018.01)
*C12Q 1/6848* (2018.01)
*C12Q 1/6806* (2018.01)

(52) U.S. Cl.
CPC ......... *C12Q 1/6848* (2013.01); *C12Q 1/6806* (2013.01)

(58) Field of Classification Search
CPC ...................................................... C12Q 1/68
See application file for complete search history.

(56) References Cited

U.S. PATENT DOCUMENTS

| | | |
|---|---|---|
| 9,957,549 B2 | 5/2018 | Armour |
| 2003/0175709 A1 | 9/2003 | Murphy et al. |
| 2005/0003369 A1 | 1/2005 | Christians et al. |
| 2005/0123987 A1 | 6/2005 | Christians et al. |
| 2006/0035256 A1 | 2/2006 | Dahlberg et al. |
| 2007/0009939 A1* | 1/2007 | Christians ............ C12Q 1/6806 435/6.11 |

(Continued)

OTHER PUBLICATIONS

Kleiboeker (Quantitative assessment of the effect of uracil-DNA glycosylase on amplicon DNA degradation and RNA amplification in reverse transcription-PCR, Virol J. 2005; 2: 29. Published online Apr. 11, 2005).*

(Continued)

*Primary Examiner* — Aaron A Priest
(74) *Attorney, Agent, or Firm* — Bret E. Field; Bozicevic, Field & Francis LLP

(57) ABSTRACT

Provided are methods of depleting a target nucleic acid in a sample. The methods include contacting a target nucleic acid with two or more polymers that specifically hybridize to the target nucleic acid, and cleaving the hybridized regions of the target nucleic acid to deplete the target nucleic acid in the sample. Kits for practicing the subject methods are also provided.

23 Claims, 11 Drawing Sheets

Specification includes a Sequence Listing.

(56) References Cited

U.S. PATENT DOCUMENTS

| | | | | |
|---|---|---|---|---|
| 2007/0031857 | A1* | 2/2007 | Makarov | C12Q 1/6855 435/6.18 |
| 2008/0102454 | A1* | 5/2008 | Wang | C12Q 1/6806 435/6.18 |
| 2008/0268508 | A1 | 10/2008 | Sowlay | |
| 2010/0297709 | A1* | 11/2010 | Rashtchian | C12Q 1/6806 435/91.3 |
| 2011/0040081 | A1 | 2/2011 | Sooknanan | |
| 2011/0111409 | A1* | 5/2011 | Sinicropi | C12Q 1/6848 435/6.11 |
| 2011/0224105 | A1* | 9/2011 | Kurn | C12P 19/34 506/26 |
| 2012/0045747 | A1* | 2/2012 | Cheung | C12Q 1/706 435/5 |
| 2014/0004569 | A1* | 1/2014 | Lambowitz | C12N 15/1096 435/91.21 |
| 2014/0303000 | A1* | 10/2014 | Armour | C12N 15/1096 506/2 |
| 2015/0087027 | A1* | 3/2015 | Makarov | C12Q 1/6806 435/91.3 |
| 2015/0299695 | A1* | 10/2015 | Uhlmann | A61P 43/00 514/44 A |

OTHER PUBLICATIONS

Weiner et al. (Kits and their unique role in molecular biology: a brief retrospective, BioTechniques 44:701-704 (25th Anniversary Issue, Apr. 2008)).*
Stratagene (Gene Characterization Kits; 1988).*
Morlan et al. (Selective Depletion of rRNA Enables Whole Transcriptome Profiling of Archival Fixed Tissue, PLoS One. 2012;7(8): e42882. Epub Aug. 10, 2012).*
Uyeno et al. (Sequence-Specific Cleavage of Small-Subunit (SSU) rRNA with Oligonucleotides and RNase H: a Rapid and Simple Approach to SSU rRNA-Based Quantitative Detection of Microorganisms, Appl Environ Microbiol. Jun. 2004;70(6):3650-63).*
Dobosy et al., "RNase H-dependent PCR (rhPCR): improved specificity and single nucleotide polymorphism detection using blocked cleavable primers". BMC Biotechnology. 11: 80. doi:10.1186/1472-6750-11-80.*
Wikipedia, Ribonuclease H, available at https://en.wikipedia.org/wiki/Ribonuclease_H, accessed Mar. 4, 2021.*
Wikipedia, Uracil-DNA glycosylase, available at https://en.wikipedia.org/wiki/Uracil-DNA_glycosylase, accessed Mar. 4, 2021.*
Anisimova et aL "Isolation, characterization and molecular cloning of Duplex-Specific Nuclease from the hepatopancreas of the Kamchatka crab," BMC Biochemistry, vol. 9, No. 14, May 21, 2008, pp. 1-12.
Castellano et al. "Deep sequencing of small RNAs identifies canonical and non-canonical miRNA and endogenous siRNAs in mammalian somatic tissues", Nucleic Acids Res. 2013; 41 (5):3339-51.
Hall et al. "Unravelling the general properties of siRNAs: strength in numbers and lessons from the past", Nat Rev Genet., Jul. 2004;5(7):552-7.
Harvey et al. "Characterization and applications of CataCleave probe in real-time detection assays", Analytical Biochemistry 333, (2004), 246-255.
MacFarlane et al. "Micro RNA: Biogenesis", Function and Role in Cancer, Current Genomics, 2010, 11, 537-561.
Morlan et al., "Selective Depletion ofrRNA Enables Whole Transcriptome Profiling of Archival Fixed Tissue", PLOS ONE, vol. 7, No. 8, e42882, pp. 1-8, 2012.
Peter "Targeting of mRNAs by multiple miRNAs: the next step", Oncogene, 2010, 29, 2161-2164.
Pratt et al. "The RNA-induced Silencing Complex: A Versatile Gene-silencing Machine", The Journal of Biological Chemistry vol. 284, No. 27, pp. 17897-17901, 2009.
Schroder et al. "Isolation and characterization of the novel polyadenylate- and polyuridylate-degrading acid andoribonuclease V from calf thymus", J Biol Chem., 1980;255(11):51 08-12.
Turner et al. "Formalin-Fixed Paraffin-Embedded Tissues Methods, in Molecular Biology", vol. 724, 2011, pp. 269-280, 2011.
Uyeno et al. "Sequence-Specific Cleavage of Small-Subunit (SSU) rRNA with Oligonucleotides and RNase H: a Rapid and Simple Approach to SSU rRNA-Based Quantitative Detection of Microorganisms", Appl Environ Microbial., 2004;70(6):3650-63.
Uyeno et al. "Evaluation of group-specific, 16S rRNA-targeted scissor probes for quantitative detection of predominant bacterial populations in dairy cattle rumen", J Appl Microbial., 2007;103(5):1995-2005.
Kleiboeker "Quantitative assessment of the effect of uracil-DNA glycosylase on amplicon DNA degradation and RNA amplification in reverse transcription—PeR", Viral J. 2005; 2: 29. Published online Apr. 11, 2005).

* cited by examiner

FIG. 7

| | |
|---|---|
| 5s1 | /5Biosg/ggtattcccaggcggtctcccatccaagta(SEQ ID NO:01) |
| 5.8s1 | /5Biosg/cacgagccgagtgatccaccgctaagagtc(SEQ ID NO:02) |
| 5.8s2 | /5Biosg/tcacattaattctcgcagctagctgcgttc(SEQ ID NO:03) |
| 5.8s3 | /5Biosg/aagtgcgttcgaagtgtcgatgatcaatgt(SEQ ID NO:04) |
| 5.8s4 | /5Biosg/gttcctcccggggctacgcctgtctgagcg(SEQ ID NO:05) |
| | |
| 18s1 | /5Biosg/gcatatgctactggcaggatcaaccaggta(SEQ ID NO:06) |
| 18s2 | /5Biosg/cgtgcgtactcagacatgcatggcttaatc(SEQ ID NO:07) |
| 18s3 | /5Biosg/aactgatttaatgagccattcgcagtttca(SEQ ID NO:08) |
| 18s4 | /5Biosg/ttatccaagtaggagaggagcgagcgacca(SEQ ID NO:09) |
| 18s5 | /5Biosg/cagcgcccgtcggcatgtattagctctag(SEQ ID NO:10) |
| 18s6 | /5Biosg/ttgatctgataaatgcacgcatcccccccg(SEQ ID NO:11) |
| 18s7 | /5Biosg/GCCGGGGCCGGAGAGGGGCTGACCGGGTTG(SEQ ID NO:12) |
| 18s8 | /5Biosg/gcccgaggttatctagagtcaccaaagccg(SEQ ID NO:13) |
| 18s9 | /5Biosg/gttcgaatgggtcgtcgccgccacgggggg(SEQ ID NO:14) |
| 18s10 | /5Biosg/gtaggcacggcgactaccatcgaaagttga(SEQ ID NO:15) |
| | |
| 18s11 | /5Biosg/ggaatcgaaccctgattccccgtcacccgt(SEQ ID NO:16) |
| 18s12 | /5Biosg/cttccttggatgtggtagccgtttctcagg(SEQ ID NO:17) |
| 18s13 | /5Biosg/cctcccggtcgggagtgggtaatttgcg(SEQ ID NO:18) |
| 18s14 | /5Biosg/gggcctcgaaagagtcctgtattgttattt(SEQ ID NO:19) |
| 18s15 | /5Biosg/tcctcgttaaaggatttaaagtggactcat(SEQ ID NO:20) |
| 18s16 | /5Biosg/AGCTGGAATTACCGCGGCTGCTGGCACCAG(SEQ ID NO:21) |
| 18s17 | /5Biosg/tttaactgcagcaactttaatatacgctat(SEQ ID NO:22) |
| 18s18 | /5Biosg/gcggaccgcccgcccgctcccaagatccaa(SEQ ID NO:23) |
| 18s19 | /5Biosg/gagaggcaaggggcggggacgggcggtggc(SEQ ID NO:24) |
| 18s20 | /5Biosg/gccccgcgggacactcagctaagagcatcg(SEQ ID NO:25) |
| 18s21 | /5Biosg/tgctttgaacactctaattttttcaaagta(SEQ ID NO:26) |
| 18s22 | /5Biosg/ttccattattcctagctgcggtatccaggc(SEQ ID NO:27) |
| 18s23 | /5Biosg/cctcagttccgaaaaccaacaaaatagaac(SEQ ID NO:28) |
| 18s24 | /5Biosg/gcgcaatacgaatgccccggccgtccctc(SEQ ID NO:29) |
| 18s25 | /5Biosg/tggtccgtcttgcgccggtccaagaatttc(SEQ ID NO:30) |
| 18s26 | /5Biosg/TAATGAAAACATTCTTGGCAAATGCTTTCG(SEQ ID NO:31) |
| 18s27 | /5Biosg/tacgacggtatctgatcgtcttcgaacctc(SEQ ID NO:32) |
| 18s28 | /5Biosg/tacgacggtatctgatcgtcttcgaacctc(SEQ ID NO:33) |
| 18s29 | /5Biosg/cgccgccgcatcgccggtcggcatcgttta(SEQ ID NO:34) |
| 18s30 | /5Biosg/TTTGCAACCATACTCCCCCCGGAACCCAAA(SEQ ID NO:35) |
| 18s31 | /5Biosg/gctccactcctggtggtgcccttccgtcaa(SEQ ID NO:36) |
| 18s32 | /5Biosg/ccgggtgaggtttcccgtgttgagtcaaat(SEQ ID NO:37) |
| 18s33 | /5Biosg/agaaagagctatcaatctgtcaatcctgtc(SEQ ID NO:38) |

FIG. 7 (cont'd)

| | |
|---|---|
| 18s34 | /5Biosg/accaactaagaacggccatgcaccaccacc(SEQ ID NO:39) |
| 18s35 | /5Biosg/agtctcgttcgttatcggaattaaccagac(SEQ ID NO:40) |
| 18s36 | /5Biosg/gccgaccgctcggggtcgcgtaactagtt(SEQ ID NO:41) |
| 18s37 | /5Biosg/gtggctgaacgccacttgtccctctaagaa(SEQ ID NO:42) |
| 18s38 | /5Biosg/catctaagggcatcacagacctgttattgc(SEQ ID NO:43) |
| 18s39 | /5Biosg/cacgctgagccagtcagtgtagcgcgcgtg(SEQ ID NO:44) |
| 18s40 | /5Biosg/gttcaacgggttacccgcgcctgccggcgt(SEQ ID NO:45) |
| 18s41 | /5Biosg/tggggaataattgcaatccccgatccccat(SEQ ID NO:46) |
| 18s42 | /5Biosg/gcaagcttatgacccgcacttactgggaat(SEQ ID NO:47) |
| 18s43 | /5Biosg/gcgacgggcggtgtgtacaaagggcaggga(SEQ ID NO:48) |
| 18s44 | /5Biosg/gccgatccgagggcctcactaaaccatcca(SEQ ID NO:49) |
| 18s45 | /5Biosg/tctcagcgctccgccagggccgtgggccga(SEQ ID NO:50) |
| 18s46 | /5Biosg/CCTTGTTACGACTTTTACTTCCTCTAGATA(SEQ ID NO:51) |
| 18s47 | /5Biosg/taatgatccttccgcaggttcacctacgg(SEQ ID NO:52) |
| 28s1 | /5Biosg/gcgggtcgccacgtctgatctgaggtcgcg(SEQ ID NO:53) |
| 28s2 | /5Biosg/ttagtttcttctcctccgctgactaatatg(SEQ ID NO:54) |
| 28s3 | /5Biosg/gctcttccctgttcactcgccgttactgag(SEQ ID NO:55) |
| 28s4 | /5Biosg/GCGCCCCGCCGCGGGGCGGGGATTCGGCGC(SEQ ID NO:56) |
| 28s5 | /5Biosg/cccacgagcggcgccggggagcgggtcttc(SEQ ID NO:57) |
| 28s6 | /5Biosg/ccgtccacgggctgggcctcgatcagaagg(SEQ ID NO:58) |
| 28s7 | /5Biosg/CCCGGCGCGCCGGGGGCCGCTACCGGCCTC(SEQ ID NO:59) |
| 28s8 | /5Biosg/cgctttgggctgcattcccaagcaacccga(SEQ ID NO:60) |
| 28s9 | /5Biosg/gtctcgtgccggtatttagccttagatgga(SEQ ID NO:61) |
| 28s10 | /5Biosg/TCAACTTTCCCTTACGGTACTTGTTGACTA(SEQ ID NO:61) |
| 28s11 | /5Biosg/ctcttaacggtttcacgccctcttgaactc(SEQ ID NO:63) |
| 28s12 | /5Biosg/tgaatcctccgggcggactgcgcggacccc(SEQ ID NO:64) |
| 28s13 | /5Biosg/GGGCCGCCGACACGGCCGGACCCGCCGCCG(SEQ ID NO:65) |
| 28s14 | /5Biosg/gggcgggtggagggtcgggaggaacgggg(SEQ ID NO:66) |
| 28s15 | /5Biosg/AGCCCGCCCCCTCCGGGGAGGAGGAGGAGG(SEQ ID NO:67) |
| 28s16 | /5Biosg/ccggccccgcccgcccaccccgcacccgc(SEQ ID NO:68) |
| 28s17 | /5Biosg/cggtcgccggtcggggacggtcccccgcc(SEQ ID NO:69) |
| 28s18 | /5Biosg/cgcggcgcaccgccgcggtggaaatgcgcc(SEQ ID NO:70) |
| 28s19 | /5Biosg/accttccccgccgggccttcccagccgtcc(SEQ ID NO:71) |
| 28s20 | /5Biosg/CGGGGGAGGAGGAGGACGGACGGACGGACG(SEQ ID NO:72) |
| 28s21 | /5Biosg/CGCCCTCCCGAGGGAGGACGCGGGGCCGGG(SEQ ID NO:73) |
| 28s22 | /5Biosg/ctcgggggggggtttcggtcccgccgccgcc(SEQ ID NO:74) |
| 28s23 | /5Biosg/ccgggattcggcgagtgctgctgccggggg(SEQ ID NO:75) |
| 28s24 | /5Biosg/GAGAGCGCGGCGACGGGTCTCGCTCCCTCG(SEQ ID NO:76) |
| 28s25 | /5Biosg/accccccctcgcggggattcccgcggggg(SEQ ID NO:77) |
| 28s26 | /5Biosg/cccccccacgaggagacgccggcgcgcccc(SEQ ID NO:78) |
| 28s27 | /5Biosg/ggggtggagagcggtcgcgccgtgggagg(SEQ ID NO:79) |
| 28s28 | /5Biosg/CCGCGCGCGGCACCCCCCCCGTCGCCGGGG(SEQ ID NO:80) |

FIG. 7 (cont'd)

| | |
|---|---|
| 28s29 | /5Biosg/gcgcactggggacagtccgccccgccccc(SEQ ID NO:81) |
| 28s30 | /5Biosg/agagaacctcccccgggcccgacggcgcga(SEQ ID NO:82) |
| 28s31 | /5Biosg/tccgccgtcccctcttcgggggacgcgcg(SEQ ID NO:83) |
| 28s32 | /5Biosg/ggggtcggcggcgacgtcggctacccaccc(SEQ ID NO:84) |
| 28s33 | /5Biosg/gcacgtgttagactccttggtccgtgtttc(SEQ ID NO:85) |
| 28s34 | /5Biosg/cattgcgccacggcggctttcgtgcgagcc(SEQ ID NO:86) |
| 28s35 | /5Biosg/ggatcccacctcggccggcgagcgcgccgg(SEQ ID NO:87) |
| 28s36 | /5Biosg/GTGGTGCGCCCTCGGCGGACTGGAGAGGCC(SEQ ID NO:88) |
| 28s37 | /5Biosg/cgtgcgctcgtgctccacctccccggcgcg(SEQ ID NO:89) |
| 28s38 | /5Biosg/ccctgcccaggcatagttcaccatctttcg(SEQ ID NO:90) |
| 28s39 | /5Biosg/ggaccgctacggacctccaccagagtttcc(SEQ ID NO:91) |
| 28s40 | /5Biosg/tcgcccctatacccaggtcggacgaccgat(SEQ ID NO:92) |
| 28s41 | /5Biosg/cttcggagggaaccagctactagatggttc(SEQ ID NO:93) |
| 28s42 | /5Biosg/gatagctggcgctctcgcagacccgacgca(SEQ ID NO:94) |
| 28s43 | /5Biosg/ctaatcattcgctttaccggataaaactgc(SEQ ID NO:95) |
| 28s44 | /5Biosg/gccgaaacgatctcaacctattctcaaact(SEQ ID NO:96) |
| 28s45 | /5Biosg/ccggctccacgccagcgagccgggcttctt(SEQ ID NO:97) |
| 28s46 | /5Biosg/gcttaccaaaagtggcccactaggcactcg(SEQ ID NO:98) |
| 28s47 | /5Biosg/ccttaacccggcgttcggttcatcccgcag(SEQ ID NO:99) |
| 28s48 | /5Biosg/aacaccttttctggggtctgatgagcgtcg(SEQ ID NO:100) |
| 28s49 | /5Biosg/tccgacttccatggccaccgtcctgctgtc(SEQ ID NO:101) |
| 28s50 | /5Biosg/ttgattcggcaggtgagttgttacacactc(SEQ ID NO:102) |
| 28s51 | /5Biosg/CGACGCTCCAGCGCCATCCATTTTCAGGGC(SEQ ID NO:103) |
| 28s52 | /5Biosg/gccgctcccgtccactctcgactgccggcg(SEQ ID NO:104) |
| 28s53 | /5Biosg/tccgacgcacaccacacgcgcgcgcgcgcg(SEQ ID NO:105) |
| 28s54 | /5Biosg/gaaggacccacaccccgccgccgccgcc(SEQ ID NO:106) |
| 28s55 | /5Biosg/AGGAGGGGAGGAGGCGTGGGGGGGGGGCG(SEQ ID NO:107) |
| 28s56 | /5Biosg/cgtagcgtccgcgggggctccgggggcgggg(SEQ ID NO:108) |
| 28s57 | /5Biosg/gcttcaaggctcaccgcagcggccctccta(SEQ ID NO:109) |
| 28s58 | /5Biosg/CCTGCGGCGGCTCCACCCGGGCCCGCGCCC(SEQ ID NO:110) |
| 28s59 | /5Biosg/cttcaaagttctcgtttgaatatttgctac(SEQ ID NO:111) |
| 28s60 | /5Biosg/gttcaactgctgttcacatggaacccttct(SEQ ID NO:112) |
| 28s61 | /5Biosg/ggaacggcgctcgcccatctctcaggaccg(SEQ ID NO:113) |
| 28s62 | /5Biosg/cgatcggccgagggcaacggaggccatcgc(SEQ ID NO:114) |
| 28s63 | /5Biosg/ccgccactccggattcggggatctgaaccc(SEQ ID NO:115) |
| 28s64 | /5Biosg/GTTACCGCACTGGACGCCTCGCGGCGCCCA(SEQ ID NO:116) |
| 28s65 | /5Biosg/TCTCCCCGGGGCTCCCGCCGGCTTCTCCGG(SEQ ID NO:117) |
| 28s66 | /5Biosg/CCATTCCAGGGCGCCCTGCCCTTCACAAAG(SEQ ID NO:118) |
| 28s67 | /5Biosg/ggaaccgcgacgctttccaaggcacgggcc(SEQ ID NO:119) |
| 28s68 | /5Biosg/TCTCCCCCGGATTTTCAAGGGCCAGCGAGA(SEQ ID NO:120) |
| 28s69 | /5Biosg/atatgggtacggcccggcgcgagatttaca(SEQ ID NO:121) |
| 28s70 | /5Biosg/caacatgccagaggctgttcaccttggaga(SEQ ID NO:122) |
| 28s71 | /5Biosg/tacggatccggcttgccgacttcccttacc(SEQ ID NO:123) |

FIG. 7 (cont'd)

| | |
|---|---|
| 28s72 | /5Biosg/cgaccgacccagcccttagagccaatccttt(SEQ ID NO:124) |
| 28s73 | /5Biosg/CGCCTCGTCCAGCCGCGGCGCGCGCCCAGC(SEQ ID NO:125) |
| 28s74 | /5Biosg/gggggtgccccgggcgtgggggggggcggcg(SEQ ID NO:126) |
| 28s75 | /5Biosg/GCGCGGGGTGGGGCGGGGGAGGGCCGCGAG(SEQ ID NO:127) |
| 28s76 | /5Biosg/ggggagagagagagagagagagggcgcggggc(SEQ ID NO:128) |
| 28s77 | /5Biosg/cacgcggcgctccccggggaggggggagg(SEQ ID NO:129) |
| 28s78 | /5Biosg/gccccctgccgccccgacccttctccccccg(SEQ ID NO:130) |
| 28s79 | /5Biosg/cgccggcccccccgggtgcccgggccccccct(SEQ ID NO:131) |
| 28s80 | /5Biosg/AAGGGCCCGGCTCGCGTCCAGAGTCGCCGC(SEQ ID NO:132) |
| 28s81 | /5Biosg/CCGGGCTCCCCGGGGGCGGCCGCGACGCCC(SEQ ID NO:133) |
| 28s82 | /5Biosg/GACGAGACGTGGGGTGGGGGGGGGGGCGCG(SEQ ID NO:134) |
| 28s83 | /5Biosg/CCGCCGCCCGACCGCTCCCCGCCCCCAGCG(SEQ ID NO:135) |
| 28s84 | /5Biosg/GGGGTAGGGCGGGGGGACGAACCGCCCCGC(SEQ ID NO:136) |
| 28s85 | /5Biosg/AGGAGGAGGGGGGAACGGGGGGCGGACGGG(SEQ ID NO:137) |
| 28s86 | /5Biosg/GCCGCGCCGAGGAGGAGGGGGGAACGGG(SEQ ID NO:138) |
| 28s87 | /5Biosg/ggcggacccggcggggggggaccggcccgcg(SEQ ID NO:139) |
| 28s88 | /5Biosg/ccggccgaggcgaggcgccgcgcggaaccg(SEQ ID NO:140) |
| 28s89 | /5Biosg/ttccctggtccgcaccagttctaagtcgg(SEQ ID NO:141) |
| 28s90 | /5Biosg/gcgggccttcgcgatgctttgttttaatta(SEQ ID NO:142) |
| 28s91 | /5Biosg/CTGGGCAGAAATCACATCGCGTCAACACCC(SEQ ID NO:143) |
| 28s92 | /5Biosg/cgtttacccgcgcttcattgaatttcttca(SEQ ID NO:144) |
| 28s93 | /5Biosg/TGGCTACCTTAAGAGAGTCATAGTTACTCC(SEQ ID NO:145) |
| 28s94 | /5Biosg/tctcgttcatccattcatgcgcgtcactaa(SEQ ID NO:146) |
| 28s95 | /5Biosg/ggctgtggtttcgctggatagtaggtaggga(SEQ ID NO:147) |
| 28s96 | /5Biosg/ggtcttctttccccgctgattccgccaagc(SEQ ID NO:148) |
| 28s97 | /5Biosg/atgtctcttcaccgtgccagactagagtca(SEQ ID NO:149) |
| 28s98 | /5Biosg/gggggggcgccggggggcctcccacttattct(SEQ ID NO:150) |
| 28s99 | /5Biosg/CGGACCCCGCCCCGGGCCCCTCGCGGGGAC(SEQ ID NO:151) |
| 28s100 | /5Biosg/aaaaacgatcagagtagtggtatttcaccg(SEQ ID NO:152) |
| 28s101 | /5Biosg/GGGCTCGCCCCCCCGCCTCACCGGGTCAGT(SEQ ID NO:153) |
| 28s102 | /5Biosg/CGCGCGGCCGGGCGCTTGGCGCCAGAAGCG(SEQ ID NO:154) |
| 28s103 | /5Biosg/aaactccccacctggcactgtccccggagc(SEQ ID NO:155) |
| 28s104 | /5Biosg/gacacctgcgttaccgtttgacaggtgtac(SEQ ID NO:156) |
| 28s105 | /5Biosg/gctccacgggaggtttctgtcctccctgag(SEQ ID NO:157) |
| 28s106 | /5Biosg/tcgtactgaaaatcaagatcaagcgagctt(SEQ ID NO:158) |
| 28s107 | /5Biosg/ggtcagaaggatcgtgaggccccgctttca(SEQ ID NO:159) |
| 28s108 | /5Biosg/tgtggtaacttttctgacacctcctgctta(SEQ ID NO:160) |
| 28s109 | /5Biosg/cgtcgctatgaacgcttggccgccacaagc(SEQ ID NO:161) |
| 28s110 | /5Biosg/caatgataggaagagccgacatcgaaggat(SEQ ID NO:162) |
| 28s111 | /5Biosg/tagtgggtgaacaatccaacgcttggtgaa(SEQ ID NO:163) |
| 28s112 | /5Biosg/cctgtctcacgacggtctaaacccagctca(SEQ ID NO:164) |
| 28s113 | /5Biosg/GGCAACAACACATCATCAGTAGGGTAAAAC(SEQ ID NO:165) |
| 28s114 | /5Biosg/caaatgtctgaacctgcggttcctctcgta(SEQ ID NO:166) |

FIG. 7 (cont'd)

| | |
|---|---|
| 28s115 | /5Biosg/gtagcttcgccccattggctcctcagccaa(SEQ ID NO:167) |
| 28s116 | /5Biosg/gattctgacttagaggcgttcagtcataat(SEQ ID NO:168) |
| 28s117 | /5Biosg/cgaggctccgcggcgctgccgtatcgttcc(SEQ ID NO:169) |
| 28s118 | /5Biosg/ccggcggggacaggcgggggaccggctatc(SEQ ID NO:170) |
| 28s119 | /5Biosg/tcccgcgcgcgcggggcgcgtggagggggg(SEQ ID NO:171) |
| 28s120 | /5Biosg/caccggaccccggtcccggcgcgcggcggg(SEQ ID NO:172) |
| 28s121 | /5Biosg/ctccggccgcgccccgtttcccaggacgaa(SEQ ID NO:173) |
| 28s122 | /5Biosg/acgaacgtgcggtgcgtgacgggcgagggg(SEQ ID NO:174) |
| 28s123 | /5Biosg/gaagcaggtcgtctacgaatggtttagcgc(SEQ ID NO:175) |
| 28s124 | /5Biosg/agcgagggagctgctctgctacgtacgaaa(SEQ ID NO:176) |
| 28s125 | /5Biosg/gacaaaccccttgtgtcgagggctgactttc(SEQ ID NO:177) |

# METHODS OF DEPLETING A TARGET NUCLEIC ACID IN A SAMPLE AND KITS FOR PRACTICING THE SAME

CROSS REFERENCE TO RELATED APPLICATIONS

This application is a divisional of U.S. patent application Ser. No. 15/217,923, filed Jul. 22, 2016, which application is a continuation of U.S. patent application Ser. No. 14/023,354, filed Sep. 10, 2013, which application, pursuant to 35 U.S.C. § 119 (e), claims priority to the filing date of the U.S. Provisional Patent Application Ser. No. 61/700,727, filed Sep. 13, 2012; the disclosures of which are herein incorporated by reference.

INTRODUCTION

Applications in biomedical research often involve the analysis of specific subsets of nucleic acids present in a complex mixture of other sequences—for example, analysis of gene expression by array hybridization, qPCR or massively parallel sequencing. If the target sequences are known, PCR with specific primer sequences can be used to amplify the desired sequences out of the mixture. In some cases, however, it may be desired to analyze multiple different sequences, perhaps where sequence information is not fully known. Messenger RNAs in eukaryotic systems, for example, may be collectively amplified and analyzed using an oligo-dT primer to initiate first strand cDNA synthesis by priming on the poly A tail, thereby reducing or avoiding contamination by unwanted nucleic acids—such as ribosomal RNAs, mitochondrial RNAs and genomic DNA. A requirement for this approach, however, is that the RNA is intact and not degraded, e.g., the poly A tails are not lost or disconnected from the body of the RNA message. Unfortunately, many otherwise useful and interesting biological specimens—such as biopsied material retained as formalin-fixed and paraffin embedded tissue samples (FFPE samples) often suffer from such degradation making oligo-dT priming impractical for such samples. Further, many interesting RNA sequences do not have poly A tails—e.g., non-coding RNAs and non-eukaryotic RNAs. In such cases, random priming can be used to generally amplify all nucleotide species in the sample. However, random priming will also result in the amplification of potentially unwanted sequences—such as genomic DNA or ribosomal RNA.

SUMMARY

Provided are methods of depleting a target nucleic acid in a sample. The methods include contacting a target nucleic acid with two or more polymers that specifically hybridize to the target nucleic acid, and cleaving the hybridized regions of the target nucleic acid to deplete the target nucleic acid in the sample. Kits for practicing the subject methods are also provided.

BRIEF DESCRIPTION OF THE FIGURES

FIG. 7 provides a list of primers used in this experiment.

DETAILED DESCRIPTION

Figure 1:
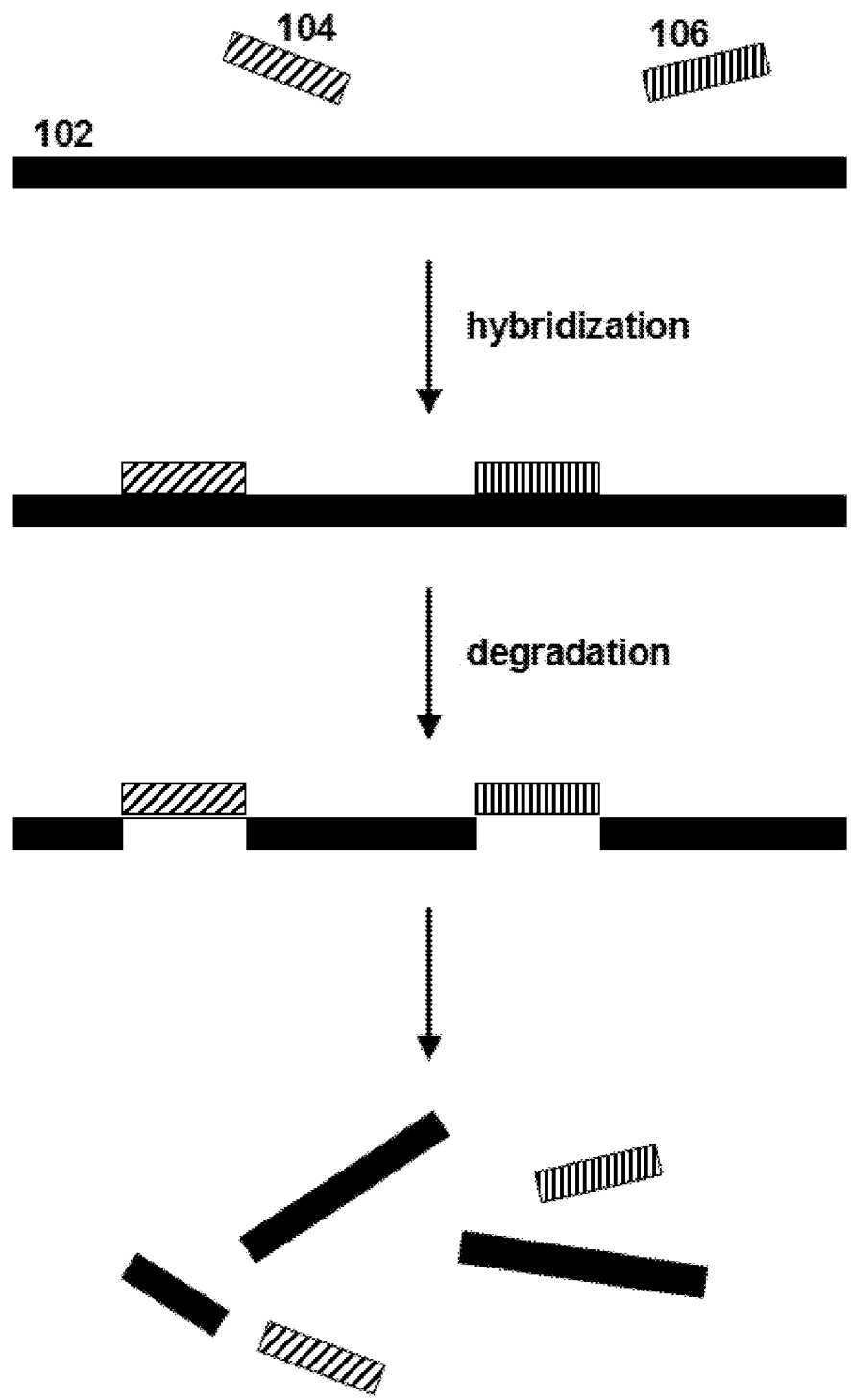
FIG. 1 schematically illustrates a method according to one embodiment of the invention.

Provided are methods of depleting a target nucleic acid in a sample. The methods include contacting a target nucleic acid with two or more polymers that specifically hybridize to the target nucleic acid, and cleaving the hybridized regions of the target nucleic acid to deplete the target nucleic acid in the sample. Kits for practicing the subject methods are also provided.

Before the methods and kits of the present disclosure are described in greater detail, it is to be understood that the methods and kits are not limited to particular embodiments described, as such may, of course, vary. It is also to be understood that the terminology used herein is for the purpose of describing particular embodiments only, and is not intended to be limiting, since the scope of the methods and kits will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the methods and kits. The upper and lower limits of these smaller ranges may independently be included in the smaller ranges and are also encompassed within the methods and kits, subject to any specifically excluded limit in the stated range. Where the stated range includes one or both of the limits, ranges excluding either or both of those included limits are also included in the methods and kits.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which the methods and kits belong. Although any methods and kits similar or equivalent to those described herein can also be used in the practice or testing of the methods, representative illustrative methods and materials are now described.

All publications and patents cited in this specification are herein incorporated by reference as if each individual publication or patent were specifically and individually indicated to be incorporated by reference and are incorporated herein by reference to disclose and describe the methods, kits and/or materials in connection with which the publications are cited. The citation of any publication is for its disclosure prior to the filing date and should not be construed as an admission that the present methods and kits are not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the methods and kits, which are, for clarity, described in the context of separate embodiments, may also be provided in combination in a single embodiment. Conversely, various features of the methods and kits, which are, for brevity, described in the context of a single embodiment, may also be provided separately or in any suitable sub-combination. All combinations of the embodiments are specifically embraced by the present invention and are disclosed herein just as if each and every combination was individually and explicitly disclosed, to the extent that such combinations embrace operable processes and/or devices/systems/kits. In addition, all sub-combinations listed in the embodiments describing such variables are also specifically embraced by the present methods and kits and are disclosed herein just as if each and every such sub-combination was individually and explicitly disclosed herein.

As will be apparent to those of skill in the art upon reading this disclosure, each of the individual embodiments described and illustrated herein has discrete components and features which may be readily separated from or combined with the features of any of the other several embodiments without departing from the scope or spirit of the present methods and kits. Any recited method can be carried out in the order of events recited or in any other order which is logically possible.

In further describing embodiments of the invention, aspects of embodiments of the subject methods will be described first in greater detail. Thereafter, aspects of embodiments of the kits for practicing the subject methods are described in greater detail.

Methods

Embodiments of the present disclosure relate to methods of depleting a target nucleic acid in a sample. The methods include contacting a target nucleic acid with two or more polymers, where each of the two or more polymers specifically hybridizes to distinct regions of the target nucleic acid to generate hybridized regions of the target nucleic acid. The methods further include cleaving the hybridized regions to deplete the target nucleic acid in the sample.

By "depleting a target nucleic acid," it is meant reducing the percentage of a type of undesired nucleic acid (e.g., ribosomal RNA (rRNA) or one or more particular sub-types thereof) in a sample with respect to the total nucleic acid in the sample. In certain aspects of the present disclosure, after depletion of the target nucleic acid, the percent remaining of the target nucleic acid as compared to the initial amount of target nucleic acid in the sample is 20%, 19%, 18%, 17%, 16%, 15%, 14%, 13%, 12%, 11%, 10%, 9%, 8%, 7%, 6%, 5%, 4%, 3%, 2%, 1%, or less, including 0.5%, 0.1%, 0.01% or less. By depleting a target nucleic acid in a sample, a desired type of nucleic acid (e.g., messenger RNA (mRNA), micro RNA (miRNA), and/or any other desired type of nucleic acid) may be enriched. According to certain embodiments, in a sample in which the target nucleic acid has been depleted, a desired type of nucleic acid is enriched such that the amount of the desired type of nucleic acid relative to the total nucleic acid in the samples increases by 5% or more, such as 10% or more, 25% or more, 30% or more, 40% or more, 50% or more, 60% or more, 70% or more, including 80%, 81%, 82%, 83%, 84%, 85%, 86%, 87%, 88%, 89%, 90%, 91%, 92%, 93%, 94%, 95%, 96%, 97%, 98%, 99%, and 99.5% or more.

The target nucleic acid is a polymer of any length composed of nucleotides, e.g., ribonucleotides or deoxyribonucleotides, e.g., 10 bases or longer, 20 bases or longer, 50 bases or longer, 100 bases or longer, 500 bases or longer, 1000 bases or longer 2000 bases or longer, 3000 bases or longer, 4000 bases or longer, 5000 bases or longer 10,000 bases or longer, 50,000 or longer or more bases.

The nucleic acid targeted for depletion can be any target nucleic acid selected by a practitioner of the subject methods. According to one embodiment, the target nucleic acid is a ribonucleic acid (RNA). The RNA targeted for depletion may be any type of RNA (or sub-type thereof) including, but not limited to, a ribosomal RNA (rRNA), a microRNA (miRNA), a messenger RNA (mRNA), transfer RNA (tRNA), a small nucleolar RNA (snoRNA), a small nuclear RNA (snRNA), a long non-coding RNA (lncRNA), a non-coding RNA (ncRNA), a small interfering RNA (siRNA), a transacting small interfering RNA (ta-siRNA), a natural small interfering RNA (nat-siRNA), a transfer-messenger RNA (tmRNA), a precursor messenger RNA (pre-mRNA), a small Cajal body-specific RNA (scaRNA), a piwi-interacting RNA (piRNA), an endoribonuclease-prepared siRNA (esiRNA), a small temporal RNA (stRNA), a signal recognition RNA, a telomere RNA, a ribozyme, and any combination of RNA types thereof or subtypes thereof. When the target nucleic acid is a RNA, the methods may include depleting all types of RNA in the sample (e.g., ribosomal RNA, transfer RNA, microRNA, and the like), or one or more particular types of RNA. In certain aspects, the target nucleic acid is ribosomal RNA (rRNA). The rRNA may be a eukaryotic 28S, 26S, 25S, 18S, 5.8S, 5S rRNA, or any combination thereof. In other aspects, the rRNA may be a prokaryotic 23S, 16S, 5S rRNA, or any combination thereof. The subject methods find use in depleting RNAs other than ribosomal RNAs. For example, the target nucleic acid may be a messenger RNA (mRNA), e.g., a highly expressed but clinically irrelevant mRNA from a pool of total RNA or mRNA (e.g., a globulin mRNA in a sample of total or polyA$^+$ blood RNA). Other types of RNA may be targeted for depletion, including a precursor messenger RNA (pre-mRNA), a micro RNA (miRNA), a transfer RNA (tRNA), a mitochondrial RNA (mtRNA), and any combination thereof. The target RNA may be a RNA from a particular organism, such as bacterial RNA or yeast RNA.

According to certain embodiments, the target nucleic acid is a DNA, e.g., intronic or inter-geneic DNA to enrich a sample for exonic DNA. DNA-based plasmids/vectors such as those used for in vitro transcription may be targeted for depletion, e.g., to enrich a nucleic acid sample for newly transcribed RNA.

The term "sample", as used herein, relates to a material or mixture of materials, typically, although not necessarily, in liquid form, containing a mixture of desired and undesired nucleic acids. A sample may be derived from any source of interest. For example, the sample may be a mixture of undesired and desired nucleic acids isolated from a biological sample such as a single cell, a plurality of cells, organelle, a tissue, an organ, or an organism(s) (e.g., bacteria, yeast, or the like). Approaches, reagents and kits for isolating DNA or RNA from such sources are known in the art. For example, kits for isolating total RNA from cells or tissues of interest—such as the NucleoSpin® RNA kits by Clontech Laboratories, Inc. (Mountain View, Calif.)—are commercially available. In certain aspects, the sample is a mixture of undesired and desired nucleic acids isolated from a fixed biological sample, e.g., formalin-fixed, paraffin-embedded (FFPE) tissue. Total RNA from FFPE tissue may be isolated using commercially available kits—such as the NucleoSpin® FFPE RNA kits by Clontech Laboratories, Inc. (Mountain View, Calif.). Kits for isolating polyA$^+$ mRNA from total RNA or directly from cells or tissue—such as the NucleoTrap® mRNA kits by Clontech Laboratories, Inc. (Mountain View, Calif.)—are commercially available. Small RNAs such as miRNAs, siRNAs, shRNAs and snRNAs may be isolated from cells, tissues or plasma using commercially available kits—such as the NucleoSpin® miRNA kits by Clontech Laboratories, Inc. (Mountain View, Calif.).

As set forth above, the subject methods include contacting the target nucleic acid with two or more polymers. The two or more polymers can be any polymer suitable for facilitating the cleavage of the target nucleic acid. Suitable polymers include, but are not limited to, nucleic acids (e.g., DNA and/or RNA of any length), proteins, and any modified variants thereof. According to certain embodiments, the two or more polymers are two or more nucleic acids. For example, the two or more polymers may be two or more DNA molecules, two or more RNA molecules, or two or more nucleic acids that include at least one DNA and at least one RNA. In certain aspects, the two or more polymers are independently selected from a DNA (e.g., a DNA oligonucleotide), an RNA (e.g., an RNA oligonucleotide), a locked nucleic acid (LNA), a peptide nucleic acid (PNA), a xeno nucleic acid (XNA), and any combination thereof.

In certain aspects, the two or more polymers are labeled. The label may be any label chosen by a practitioner of the subject methods. Labels that find use in the subject methods include, but are not limited to, biotin, streptavidin, avidin, a fluorescent dye, a chromophores (e.g., a donor chromophore or acceptor chromophore capable of participating in fluorescence resonance energy transfer (FRET), and/or the like). In certain aspects, the two or more polymers are nucleic acid polymers that are incapable of serving as primers in nucleic acid extension reactions. For example, the nucleic acid polymers may have an amino group at their 3' ends to preclude priming of a nucleic acid synthesis reaction from the polymers.

According to certain embodiments, the two or more polymers are two or more oligonucleotides. By "oligonucleotide" is meant a single-stranded multimer of nucleotides from 2 to 500 nucleotides, e.g., 2 to 200 nucleotides. Oligonucleotides may be synthetic or may be made enzymatically, and, in some embodiments, are under 10 to 50 nucleotides in length. Oligonucleotides may contain ribonucleotide monomers (i.e., may be oligoribonucleotides or "RNA oligonucleotides") or deoxyribonucleotide monomers (i.e., may be oligodeoxyribonucleotides or "DNA oligonucleotides"). Oligonucleotides may be 10 to 20, 11 to 30, 31 to 40, 41 to 50, 51-60, 61 to 70, 71 to 80, 80 to 100, 100 to 150 or 150 to 200, up to 500 or more nucleotides in length, for example.

Each of the two or more polymers is provided in the sample at any final concentration suitable for the desired extent of target nucleic acid depletion. For example, the final quantity concentration of each polymer may independently be, in certain instances, from 100 nM to 100, such as 250 nM to 5 µM, including 500 nM to 2.50.

Each of the two or more polymers may specifically hybridizes to distinct regions of the target nucleic acid. By "specifically hybridizes" is meant the ability of a polymer (e.g., an oligonucleotide) to hybridize to a region of the target nucleic acid. In some instances, the polymer hybridizes, if at all, to non-target nucleic acids only partially or weakly and in some instances the targeting nucleic acid does not hybridize to any nucleic acid other than to the target nucleic acid. Whether a polymer specifically hybridizes to a target nucleic acid is determined by such factors as the degree of complementarity between the polymer and the target nucleic acid and the temperature at which the hybridization occurs, which may be informed by the melting temperature ($T_M$) of the polymer. The melting temperature refers to the temperature at which half of the polymer-target nucleic acid duplexes remain hybridized and half of the duplexes dissociate into single strands. The $T_m$ of a duplex may be experimentally determined or predicted using the following formula $T_m=81.5+16.6(\log_{10}[Na^+])+0.41$ (fraction G+C)−(60/N), where N is the chain length and [Na$^+$] is less than 1 M. See Sambrook and Russell (2001; Molecular Cloning: A Laboratory Manual, 3$^{rd}$ ed., Cold Spring Harbor Press, Cold Spring Harbor N.Y., Ch. 10). Other more advanced models that depend on various parameters may also be used to predict $T_m$ of polymer duplexes may also be used depending on various hybridization conditions. Approaches for achieving specific nucleic acid hybridization may be found in, e.g., Tijssen, Laboratory Techniques in Biochemistry and Molecular Biology-Hybridization with Nucleic Acid Probes, part I, chapter 2, "Overview of principles of hybridization and the strategy of nucleic acid probe assays," Elsevier (1993).

The term "complementary" as used herein refers to a polymer sequence (e.g., a nucleic acid polymer sequence) that base-pairs by non-covalent bonds to a target nucleic acid. In the canonical Watson-Crick base pairing, adenine (A) forms a base pair with thymine (T), as does guanine (G) with cytosine (C) in DNA. In RNA, thymine is replaced by uracil (U). As such, A is complementary to T and G is complementary to C. In RNA, A is complementary to U and vice versa. Typically, "complementary" refers to a nucleotide sequence that is at least partially complementary. The term "complementary" may also encompass duplexes that are fully complementary such that every nucleotide in one strand is complementary to every nucleotide in the other strand in corresponding positions. In certain cases, a nucleotide sequence may be partially complementary to a target, in which not all nucleotide is complementary to every nucleotide in the target nucleic acid in all the corresponding positions. For example, the polymer may be perfectly (i.e., 100%) complementary to the target nucleic acid, or the polymer and the target nucleic acid may share some degree of complementarity which is less than perfect (e.g., 70%, 75%, 85%, 90%, 95%, 99%). The percent identity of two nucleotide sequences can be determined by aligning the sequences for optimal comparison purposes (e.g., gaps can be introduced in the sequence of a first sequence for optimal alignment). The nucleotides at corresponding positions are then compared, and the percent identity between the two sequences is a function of the number of identical positions shared by the sequences (i.e., % identity=# of identical positions/total # of positions×100). When a position in one sequence is occupied by the same nucleotide as the corresponding position in the other sequence, then the molecules are identical at that position. A non-limiting example of such a mathematical algorithm is described in Karlin et al., Proc. Natl. Acad. Sci. USA 90:5873-5877 (1993). Such an algorithm is incorporated into the NBLAST and XBLAST programs (version 2.0) as described in Altschul et al., Nucleic Acids Res. 25:389-3402 (1997). When utilizing BLAST and Gapped BLAST programs, the default parameters of the respective programs (e.g., NBLAST) can be used. In one aspect, parameters for sequence comparison can be set at score=100, wordlength=12, or can be varied (e.g., wordlength=5 or wordlength=20).

Generating polymers for practicing the subject methods may include identifying unique regions of the target nucleic acid and synthesizing nucleic acid polymers (e.g., two or more oligonucleotides) that are complementary (e.g., perfectly complementary) to the unique regions. By "unique region" is meant a nucleic acid sequence within the target nucleic acid that is not present in any other nucleic acids in the sample of interest. In certain aspects, the unique regions are regions in a ribosomal RNA (e.g., a eukaryotic 28S, 26S, 25S, 18S, 5.8S, or 5S rRNA). Sequence analysis (e.g., a BLAST search) may be performed to determine which regions of a target nucleic acid are unique with respect to the sample of interest. Once the unique regions are identified, nucleic acid polymers of sufficient complementarity, length and/or G:C content may be synthesized such that the polymers specifically hybridize to the unique regions.

The hybridization step can be carried out at any suitable temperature and may be selected depending on, e.g., the minimum temperature required for specific hybridization. Suitable hybridization temperatures may range from 35° C. to 45° C., from 45° C. to 50° C., from 50° C. to 60° C., or from 60° C. to 65° C. Also of interest are lower hybridization temperatures, e.g., where the temperature of the solution is rapidly decreased, e.g., to 30° C. or less, such as 25° C. or less, 20° C. or less, 15° C., 10° C. or less, 5° C. or less, e.g., where the solution is heated and then placed on ice. The temperature of the hybridization step may be the same or different as compared to the temperature of the cleaving step. For example, in certain aspects, the hybridized regions are cleaved enzymatically, and specific hybridization of the oligonucleotides to the target nucleic acid occurs at a temperature at which the enzyme is active and capable of cleaving the hybridized regions (e.g., 37° C., 42° C., 72° C., or the like).

By "two or more polymers" is meant any number of polymers (e.g., nucleic acid polymers) greater than one polymer. In certain aspects, the target nucleic acid is contacted with 2, 3, 4, 5, 6, 7, 8, 9, 10, 15, 20, 30, 40, 50, 100, 500, or 1000 or more polymers. One practicing the subject methods may select the number of polymers based on the size and number of different target nucleic acids to be depleted (if one desires to deplete more than one target nucleic acid in the sample) and the desired extent of target nucleic acid cleavage—where the number of polymers that hybridize to distinct regions of the target nucleic acid may be increased to increase the extent of cleavage. The polymers may specifically hybridize to one particular target nucleic acid (e.g., a eukaryotic 28S, 18S, 5.8S, or 5S ribosomal RNA), or two or more different target nucleic acids (e.g., any combination of two or more eukaryotic ribosomal RNAs selected from 28S, 18S, 5.8S, and 5S ribosomal RNA). For example, the subject methods can be used to concurrently deplete the 28S and 18S populations of eukaryotic rRNAs in a sample using a polymer cocktail that includes two or more nucleic acid polymers that specifically hybridize to 28S rRNAs and two or more nucleic acid polymers that specifically hybridize to 18S rRNAs.

In certain embodiments, the target nucleic acid is denatured prior to hybridization of the two or more polymers to the target nucleic acid. The denaturation step may be useful for removing any secondary structure in a target RNA or for separating the two strands of a double-stranded target DNA, thereby ensuring the availability of the distinct regions of the target nucleic for hybridization to the polymers. When the method includes a denaturation step, the denaturation may be performed at a temperature and for a duration suitable to denature the target nucleic acid. The denaturation temperature, for example, may be selected according to the length of the target nucleic acid, the GC content of the target nucleic acid (or relevant sub-region thereof), and/or the like. In certain aspects, the methods include denaturing the target nucleic acid at a temperature of from 50° C. to 98° C., from 55° C. to 95° C., from 60° C. to 90° C., or from 70° C. to 80° C., for example. Denaturing, when employed, may also be accomplished by other protocols, e.g., chemical treatment, such as treatment with NaOH.

Upon specific hybridization of the two or more polymers to the distinct regions of the target nucleic acid, the subject methods include cleaving the hybridized regions of the target nucleic acid to deplete the target nucleic acid in the sample. In certain aspects, the cleaving is performed by contacting the hybridized regions with an enzyme. Approaches for enzymatic cleavage of the hybridized regions of the target nucleic acid may depend on the nature of the hybridized region. In certain aspects, the target nucleic acid is an RNA (e.g., a ribosomal RNA), and the two or more polymers are two or more DNAs (e.g., two or more DNA oligonucleotides). In this example, the hybridized regions constitute DNA/RNA duplexes at the distinct regions of the target RNA, and the cleaving may be carried out by contacting the DNA/RNA duplexes with a ribonuclease that specifically cleaves RNA present in a DNA/RNA duplex, such as RNase H. In other aspects, the target nucleic acid is a DNA, and the two or more polymers are two or more RNAs (e.g., two or more RNA oligonucleotides). Here, the hybridized regions constitute DNA/RNA duplexes at the distinct regions of the target DNA, and the cleaving may be carried out by contacting the DNA/RNA duplexes with an enzyme that specifically cleaves DNA present in a DNA/RNA duplex. In other aspects, the target nucleic acid is an RNA and the two or more polymers are RNA polymers. In this aspect, the target RNA of the resulting RNA/RNA duplex may be cleaved using an enzyme that specifically cleaves an RNA in an RNA/RNA duplex, such as RNase V1.

Enzymes that find use in practicing the subject methods are commercially available and include, but are not limited to: RNAse H, RNase V, duplex-specific nuclease (DSN), lambda exonuclease, T7 exonuclease, exonuclease III, RecJ$_f$ exonuclease I, exonuclease T, exonuclease V, BAL-31 nuclease, mung bean nuclease, DNase I, micrococcal nuclease, T7 endonuclease I, T5 exonuclease, and any combination thereof. Information regarding nucleases and their substrates is found, e.g., in Mishra et al. (Nucleases: Molecular Biology and Applications (ISBN: 978-0-471-39461-7), the disclosure of which is incorporated herein in its entirety for all purposes. Additional nucleases of interest include, but are not limited to: RNase V1 (e.g., for cleavingdsRNA), oligoribonucleases, (e.g., for cleaving oligonucleotides), exoribonuclease II (e.g., for cleaving mature miRNAs), etc.

The cleaving step may produce a fragmented target nucleic acid, the fragments of which may be removed from the sample if desired. In certain embodiments, the number of the polymers used, the length of the polymers and/or the locations of the distinct regions of the target nucleic acid to which the polymers bind are selected such that all or nearly all of the target nucleic acid fragments are sufficiently small to be removed by nucleic acid purification steps such as ethanol or isopropanol precipitation, spin column purification (e.g., using NucleoSpin® Clean-Up columns by Clontech Laboratories, Inc. (Mountain View, Calif.)), or the like.

A method according to one embodiment of the present disclosure is schematically illustrated in FIG. 1. Nucleic acid polymers 104 and 106 specifically hybridize to distinct regions of target nucleic acid 102. Upon hybridization of the polymers to the target nucleic acid, the hybridized regions of the target nucleic acid are cleaved to deplete the target nucleic acid in the sample.

Methods of the invention may further include removing the two or more polymers from the sample. For example, a strategy for removing target nucleic acid fragments from the sample (e.g., alcohol precipitation, column purification, or the like) may also be useful for concurrently removing the two or more polymers from the sample, where the polymers are suitable (e.g., sufficiently small) to be removed by the purification approach employed. Alternatively, or additionally, the polymers may be degraded after the hybridized regions of the target nucleic acid are cleaved. In certain aspects, after cleaving the hybridized regions, at least one of the two or more polymers are contacted with an enzyme. The enzyme may be an enzyme (e.g., a nuclease) that specifically cleaves that particular type of polymer (e.g., a DNA, an RNA, or the like). For example, when the target nucleic acid is an RNA and two or more DNA polymers are used, the DNA polymers may be cleaved using a nuclease that specifically cleaves DNA (and not RNA), such as exonuclease I, DNase I, a ribozyme, or any combination thereof.

Other approaches for removing the two or more polymers are possible. According to one embodiment, the polymer is a nucleic acid polymer that includes one or more nucleotides that are not normally present in a DNA or RNA molecule, where the nucleotide not normally present marks the polymer for cleavage when the polymers is contacted with a particular enzyme. For example, the triphosphate form of deoxyuridine (dUTP) is present in living organisms as a metabolic intermediate, but it is rarely incorporated into DNA. When dUTP is incorporated into DNA, the resulting deoxyuridine is promptly removed in vivo, e.g. by processes involving the enzyme uracil-N-glycosylase (UDG). In certain aspects, the subject methods employ a DNA polymer in which dUTP is incorporated into the polymer. Following the target nucleic acid cleavage step of the subject methods, the uracil-containing polymer may be contacted with UDG, which cleaves the glycosidic bond between the deoxyribose of the DNA sugar-phosphate backbone and the uracil base, effectively degrading the polymer and/or facilitating their subsequent removal by alcohol precipitation, spin column purification, or other suitable removal strategies.

Also of interest in certain embodiments is the use of a physical separation protocol for removing the polymers from the resultant sample in which the target nucleic acid has been degraded. Any convenient physical separation protocol that selectively removes the polymers from the sample may be employed. An example of a physical separation protocol is one that relies of on specific binding of the polymers to a solid phase, where the solid phase is then separate from sample, thereby physically separating the polymers from the sample. For example, the polymers may be tagged, e.g., with biotin, an oligonucleotide tag, etc., and the contacted with a solid phase comprising a specific binding member for the tag, e.g., avidin where the tag is biotin, a complementary oligo where the tag is an oligonucleotide, etc. The solid phase may vary, where solid phases of interest include, but are not limited to: beads, including magnetic beads, an array, etc.

Turning now to more specific applications of the protocols described herein, according to one embodiment of the present disclosure, a method of depleting ribosomal RNA in a total RNA sample is provided. The method includes contacting a target rRNA with two or more DNA polymers (e.g., two or more DNA oligonucleotides) that specifically hybridize to distinct regions of the target rRNA to generate hybridized regions of the target rRNA. In this embodiment, the DNA polymers are synthesized with dUTP instead of dTTP, and accordingly, have dUTP incorporated therein. The method further includes cleaving the hybridized regions by treatment with RNase H, and subsequently cleaving the DNA polymers by treatment with uracil-N-glycosylase (UDG). After cleavage of the target rRNA and DNA polymers, RNAs are optionally synthesized via a polymerase extension reaction in which random oligonucleotides are used as primers.

In certain aspects, a method of depleting ribosomal RNA in a total RNA sample is provided. The method includes contacting a target rRNA with two or more DNA polymers (e.g., two or more DNA oligonucleotides) that specifically hybridize to distinct regions of the target rRNA to generate hybridized regions of the target rRNA. The method further includes cleaving the hybridized regions by treatment with RNase H, and subsequently cleaving the DNA polymers by treatment with exonuclease I. After cleavage of the target rRNA and DNA polymers, RNAs are optionally synthesized via a polymerase extension reaction in which random oligonucleotides are used as primers.

According to one embodiment, a method of depleting ribosomal RNA in a total RNA sample is provided. The method includes contacting a target rRNA with two or more DNA polymers (e.g., two or more DNA oligonucleotides) that specifically hybridize to distinct regions of the target rRNA to generate hybridized regions of the target rRNA. Reverse transcriptase and dNTPs are then added to the sample and cDNA synthesis using the DNA polymers as primers is performed. The cDNA synthesis reaction generates hybrids between the newly-synthesized cDNA and the target rRNA. The regions of the target rRNA that are hybridized to the DNA polymers and newly-synthesized cDNA is then cleaved by treatment with RNase H. The DNA polymers/cDNA is then cleaved by treatment a suitable enzyme, e.g., with DNase, ExoI, etc. After cleavage of the target rRNA and DNA polymers/cDNA, RNAs are optionally synthesized via a polymerase extension reaction in which random oligonucleotides are used as primers.

In certain aspects, a method of depleting ribosomal RNA in a total RNA sample is provided. The method includes contacting a target rRNA with two or more oligonucleotides (e.g., DNA oligonucleotides) that specifically hybridize to distinct regions of the target rRNA to generate hybridized regions of the target rRNA. The method further includes cleaving the hybridized regions by treatment with RNase H. Following RNase H treatment, the oligonucleotides are separated from the remaining RNA in the sample by one of two approaches. First, the oligonucleotides may be removed from the sample by ethanol precipitation, by peg precipitation, by SPRI beads, etc. Alternatively, the remaining RNA in the sample may be collected by running the sample through an RNA binding column. Once the non-cleaved RNA is separated from the oligonucleotides, RNAs are optionally synthesized via a polymerase extension reaction in which random oligonucleotides are used as primers.

Kits

Also provided by the present disclosure are kits useful for practicing the subject methods. The kits include two or more polymers, where each of the two or more polymers specifically hybridize to distinct regions of a target nucleic acid. The kits further include a nuclease capable of specifically cleaving the distinct regions of the target nucleic acid when the two or more polymers are hybridized to the target nucleic acid. polymers The two or more polymers included in the kit may be configured to specifically hybridize (e.g., are complementary) to distinct regions of a target RNA or a target DNA. In certain embodiments, the target nucleic acid is an RNA. The RNA may be a ribosomal RNA, a microRNA, a messenger RNA, a precursor messenger RNA, a transfer RNA, or a mitochondrial RNA, and the polymers may be DNA polymers. Such kits may include a nuclease that specifically cleaves RNA present in a DNA/RNA duplex (e.g., RNase H), compatible buffers for carrying out the cleavage reaction, and/or the like. In certain aspects, the target nucleic acid is a ribosomal RNA (e.g., an rRNA selected from a eukaryotic 28S, 26S, 25S, 18S, 5.8S, or 5S rRNA, an rRNA from prokaryotic sources, etc.), and the kits include two or more DNA polymers configured to specifically hybridize to the ribosomal RNA. In other aspects, the target nucleic acid is an RNA and the two or more polymers are RNA polymers. A kit according to this embodiment may include an enzyme that specifically cleaves an RNA present in an RNA/RNA duplex (e.g., RNase V), compatible buffers for carrying out the cleavage reaction, and/or the like. In some embodiments, the target nucleic acid is a DNA, and the kits include two or more RNA polymers configured to specifically hybridize to the DNA. Such kits may include a nuclease that specifically cleaves DNA present in a DNA/RNA duplex, compatible buffers for carrying out the cleavage reaction, and/or the like.

The subject kits may include any of the polymers or other reagents provided above in the description of the subject methods. Reagents, such as nucleases (e.g., exonuclease I, DNase I, a ribozyme, etc.), may be included in the subject kits for removal of the polymers after a cleaving step is carried out. When the kit includes polymers (e.g., DNA oligonucleotides) that include dUTP as one or more of its polymers, the kit may include uracil-N-glycosylase (UDG) to facilitate cleavage and/or removal of the oligonucleotides from the sample following cleavage of the target nucleic acid. The kits may also include reagents for performing precipitation reactions and/or spin purification columns to remove fragmented target nucleic acids and/or the two or more polymers from the sample, e.g., after a cleavage step is carried out. The subject kits may further include physical separation components, e.g., solid supports, such as beads or arrays, etc.

In certain embodiments, the kits include reagents for isolating a nucleic acid sample from a nucleic acid source. The reagents may be suitable for isolating nucleic acid samples from a variety of sources including single cells, cultured cells, tissues, organs, or organisms. The subject kits may include reagents for isolating a nucleic acid sample from a fixed cell, tissue or organ, e.g., formalin-fixed, paraffin-embedded (FFPE) tissue. Such kits may include one or more deparaffinization agents, one or more agents suitable to de-crosslink nucleic acids, and/or the like.

Components of the subject kits may be present in separate containers, or multiple components may be present in a single container. For example, the two or more polymers may be provided in separate containers, or may be provided in a single container.

In addition to above-mentioned components, the subject kit may further include instructions for using the components of the kit to practice the subject method. The instructions for practicing the subject method are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, Hard Disk Drive (HDD) etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Utility

The subject methods and kits find use in a variety of different applications where, e.g., it is desirable to deplete irrelevant and/or undesired nucleic acids from a nucleic acid sample. By depleting the irrelevant and/or undesired nucleic acids, the complexity of the sample is reduced and the sample is enriched for nucleic acids of interest. Reduced complexity and enrichment of nucleic acids of interest may facilitate and/or improve the results of downstream applications such as nucleic acid amplification, nucleic acid sequencing, gene expression analysis (e.g., by array hybridization, quantitative RT-PCR, massively parallel sequencing, etc.), the preparation of pharmaceutical compositions in which a therapeutic nucleic acid of interest is to be included, and any other applications in which reduced sample complexity and enrichment of nucleic acids of interest is beneficial.

As just one example, the subject methods and kits find use in facilitating gene expression analysis in nucleic acid samples derived from a nucleic acid source (e.g., a formalin fixed, paraffin-embedded tissue sample) in which the integrity of nucleic acids of interest (e.g., mRNAs) is often compromised. For example, the poly-A tails of mRNAs in formalin fixed, paraffin-embedded tissue samples are often absent or degraded to an extent that such tails do not support oligo-dT priming. Accordingly, if the method for enriching the nucleic acid sample for mRNAs is amplification by oligo-dT priming, a substantial proportion of the mRNAs present in the initial sample will not be amplified. The subject methods constitute an approach for enriching nucleic acids of interest that are less sensitive to sample degradation, e.g., because the undesired nucleic acids may be degraded in a manner that utilizes internal sequences of the undesired nucleic acids, which are more likely to remain intact in degraded samples as compared to the poly-A tails of mRNAs.

The following examples are offered by way of illustration and not by way of limitation.

Experimental

I. Experimental Methods:
A. Targeting Primers
60mer for 5S (with M13R sequence)

(SEQ ID NO: 178)
5'-aagtactaaccaggcccgaccctgcttagcttccgaggtcatagctg tttcctgtgtga-3'

3×30mers for 5S (SEQ ID NO: 179)
5'-aagcctacagcacccggtattcccaggcgg-3'

(SEQ ID NO: 180)
5'-aagtactaaccaggcccgaccctgcttagc-3'

(SEQ ID NO: 181)
5'-agacgagatcgggcgcgttcagggtggtat-3'

4×20mer for 5' biotinylated for 5S (SEQ ID NO: 182)
5'-biotin-aagcctacagcacccggtat-3'

(SEQ ID NO: 183)
5'-biotin-tctcccatccaagtactaac-3'

(SEQ ID NO: 184)
5'-biotin-cctgcttagcttccgagatc-3'

(SEQ ID NO: 185)
5'-biotin-gggcgcgttcagggtggtat-3'

4×30mers for 5.8S (SEQ ID NO: 186)
5'-cacgagccgagtgatccaccgctaagagtc-3'

(SEQ ID NO: 187)
5'-tcacattaattctcgcagctagctgcgttc-3'

(SEQ ID NO: 188)
5'-aagtgcgttcgaagtgtcgatgatcaatgt-3'

(SEQ ID NO: 189)
5'-gttcctcccggggctacgcctgtctgagcg-3'

B. Oligo Annealing
One µg of RNA was mixed with DTT (final concentration 1 mM), SmartScribe Buffer (final concentration 1×), and primer cocktail (final concentration of primers is 10 µM). Add water until the volume is 18 µl. Heat solution to 70° C. for 2 minutes, 37° C. for 2 minutes, 25° C. for 2 minutes, then place on ice for 2 minutes.

C. RNase H Treatment
Dilute Takara RNase H to 0.6 U/µl in water, add 1 µl to sample, along with 1 µl of RNase Inhibitor (Takara). If this is the only enzymatic reaction performed, then incubate solution at 37° C. for 90 minutes. If adding an Exo or DNaseI treatment, only incubate for 1 hour.

D. ExoI Treatment
After RNase H treatment, add 1 µl (5 U/µl) of ExoI (Takara) and incubate at 37° C. for 30 minutes.

E. Heat Inactivation
If heat inactivating the RNaseH and ExoI enzymes, add EDTA (final concentration of 5 mM) and incubate at 80° C. for 20 minutes. Transfer to ice and proceed to reverse transcriptase reaction.

F. SPRI bead purification
Follow the instructions for the Beckman Coulter Agencourt AMPure XP kit. Elute with 30 µl of water and proceed to reverse transcriptase reaction.

G. Streptavidin Purification
Wash 12.5 µl of streptavidin magnetic beads (made at Clontech, 300 ng streptavidin/µl of beads) with 500 µl or 1 ml of Tris buffer, pH 7.4. Add sample solution to washed beads and incubate at 4° C. with rotation for 30 minutes. Remove supernatant (about 25 µl) and proceed to reverse transcriptase reaction.

H. Reverse Transcriptase Reaction
Take 2-3 µl of sample after heat activation and/or purification and perform a reverse transcriptase reaction with SMARTScribe protocol (Clontech), using a N6 random primer. Proceed to qPCR reactions.

II. Results
A. A Targeting Primer and RNase H Treatment Selectively Depleted the Target RNA and Exonuclease Treatment Depleted the Targeting Primer.

Figure 2:
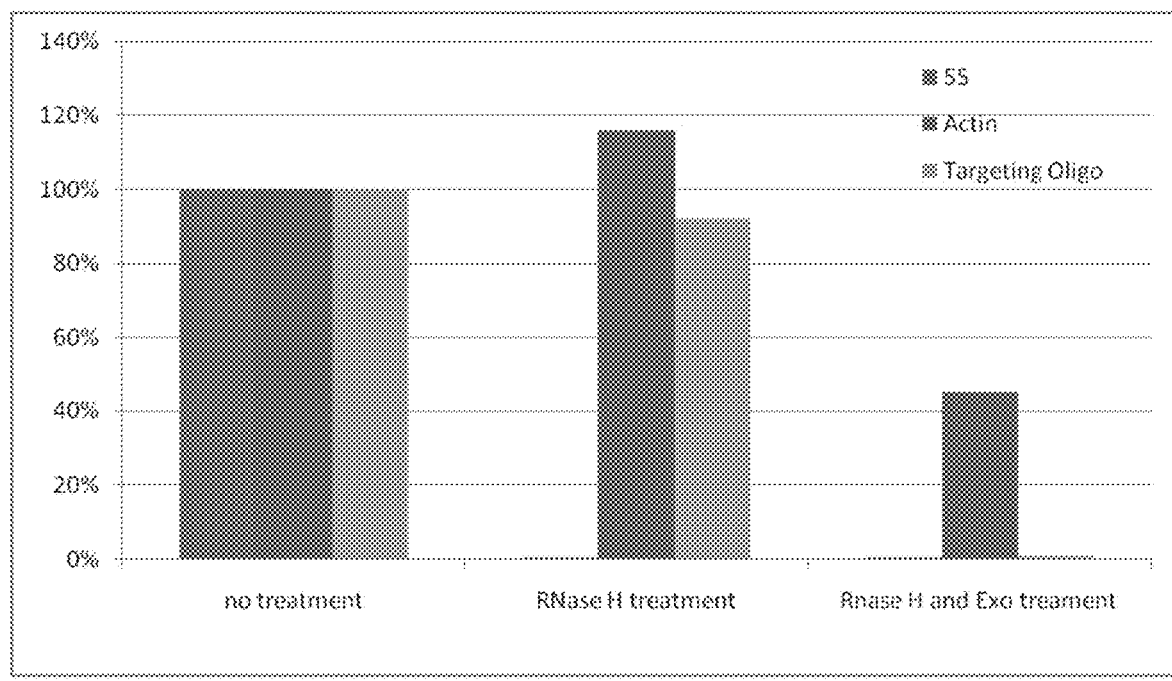
FIG. 2 shows the graphical results from an experiment in which a targeting primer and RNase H treatment selectively depleted the target RNA and Exonuclease treatment depleted the targeting primer, according to any embodiment of the invention.

Total mouse RNA was annealed to a single sixty nucleotide primer which hybridized to the middle of the 5S transcript. The results are shown in FIG. 2. Samples were either untreated (left), treated with RNase H alone (middle), or RNase H and Exonuclease I (right). Remaining RNA was heat inactivated, converted to cDNA with random primers, and amplified by qPCR with primers specific for the 5S (blue), Actin (red), or targeting oligo (green). All sample data are presented as a percentage of the amplification by the same primers in the untreated sample (left). Actin was included to represent the effect of the treatment overall mRNA levels.

B. A Targeting Primer and RNase H Treatment Selectively Depleted the Target RNA.

Figure 3:
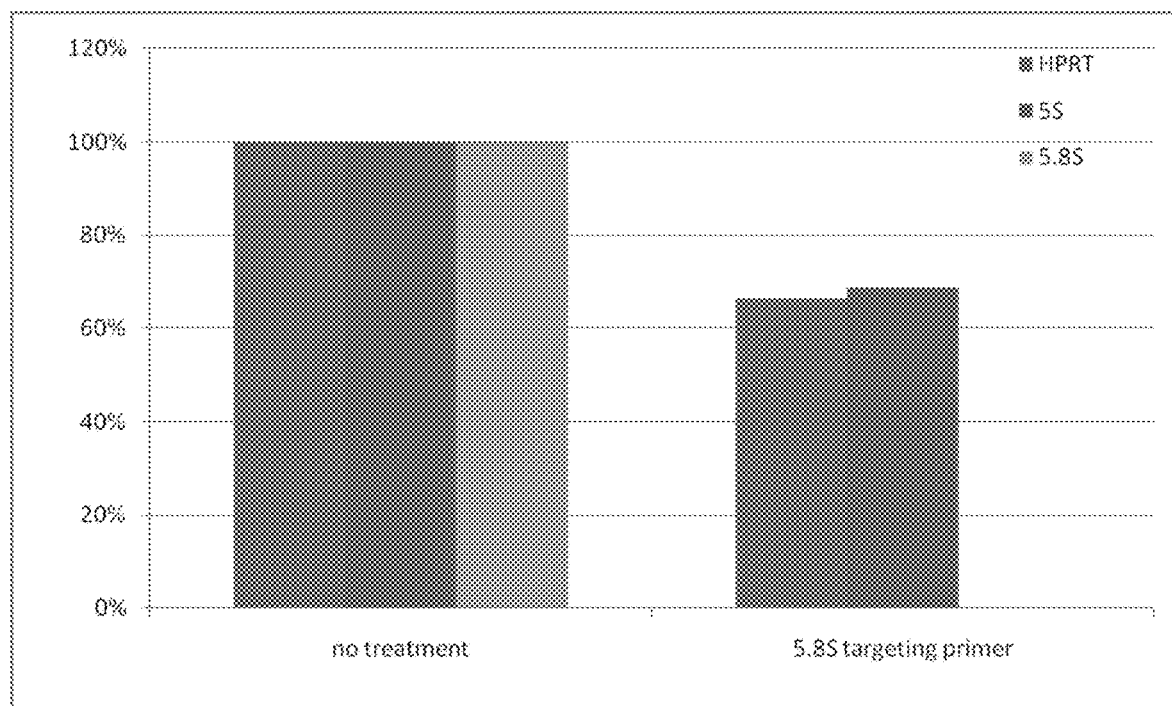
FIG. 3 shows the graphical results from an experiment in which a targeting primer and RNase H treatment selectively depleted the target RNA, according to any embodiment of the invention.

Total human universal RNA was annealed to four, thirty nucleotide primers which hybridized along the length of the 5.8S transcript. The results are shown in FIG. 3. Samples were either untreated (left) or treated with RNase H (right). Remaining RNA was purified with SPRI beads, converted to cDNA with random primers, and amplified by qPCR with primers specific for the HPRT (blue), 5S (red), or 5.8S (green). All sample data are presented as a percentage of the amplification by the same primers in the untreated sample (left). HPRT and 5S were included to represent the specificity of the targeting primer treatment.

C. The Targeting Primer is Capable of Selectively Depleting 5S Transcripts at a Range of Concentrations.

Figure 4:
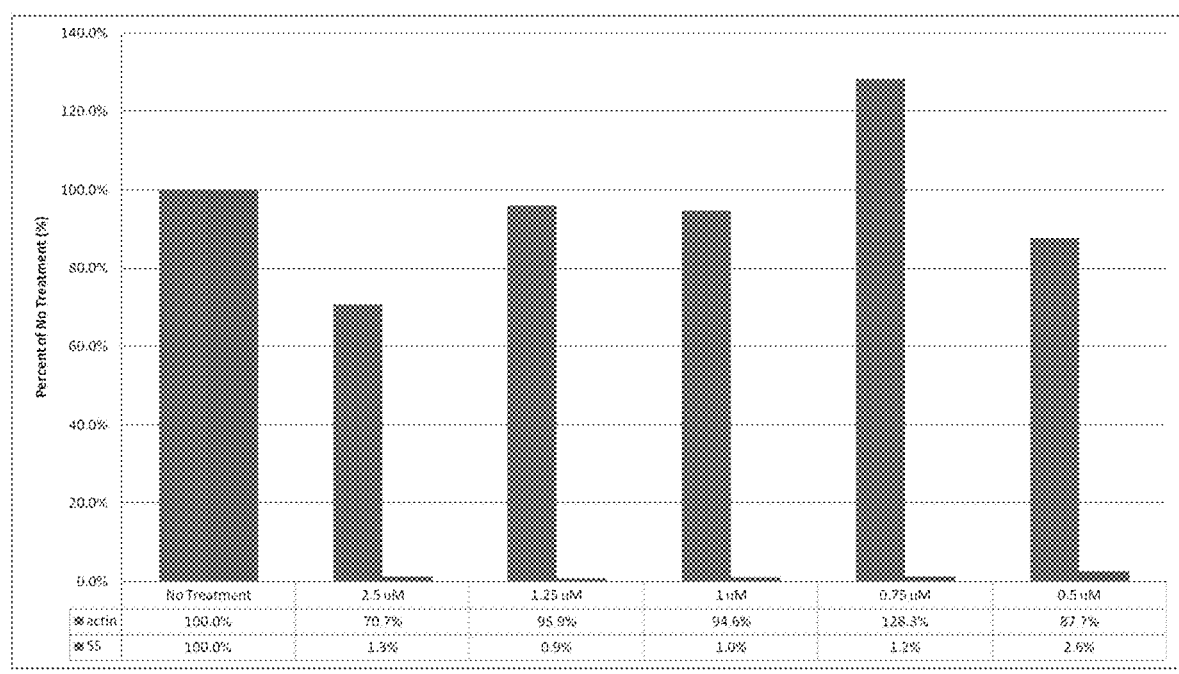
FIG. 4 shows the graphical results from an experiment demonstrating that a targeting primer is capable of selectively depleting 5S transcripts at a range of concentrations, when employed in methods according to an embodiment of the invention.

Total mouse RNA was annealed to four, twenty nucleotide, biotinylated primers which hybridized along the length of the 5S transcript. The results are shown in FIG. 4. Samples were either untreated (no primer, left) or treated with a range of targeting primer concentrations (2.5 µM, 1.25 µM, 1 µM, 0.75 µM, or 0.5 µM). All samples were then treated with RNase H, and the remaining RNA was separated from the biotinylated targeting primers with streptavidin-coated beads, converted to cDNA with random primers, and amplified by qPCR with primers specific for Actin (blue) or 5S (red). All sample data are presented as a percentage of the amplification by the same primers in the untreated sample (left). Actin was included to represent the effect of the treatment overall mRNA levels.

D. The Targeting Primer is Capable of Selectively Depleting 5S Transcripts at a Range of Total RNA Amounts.

Figure 5:
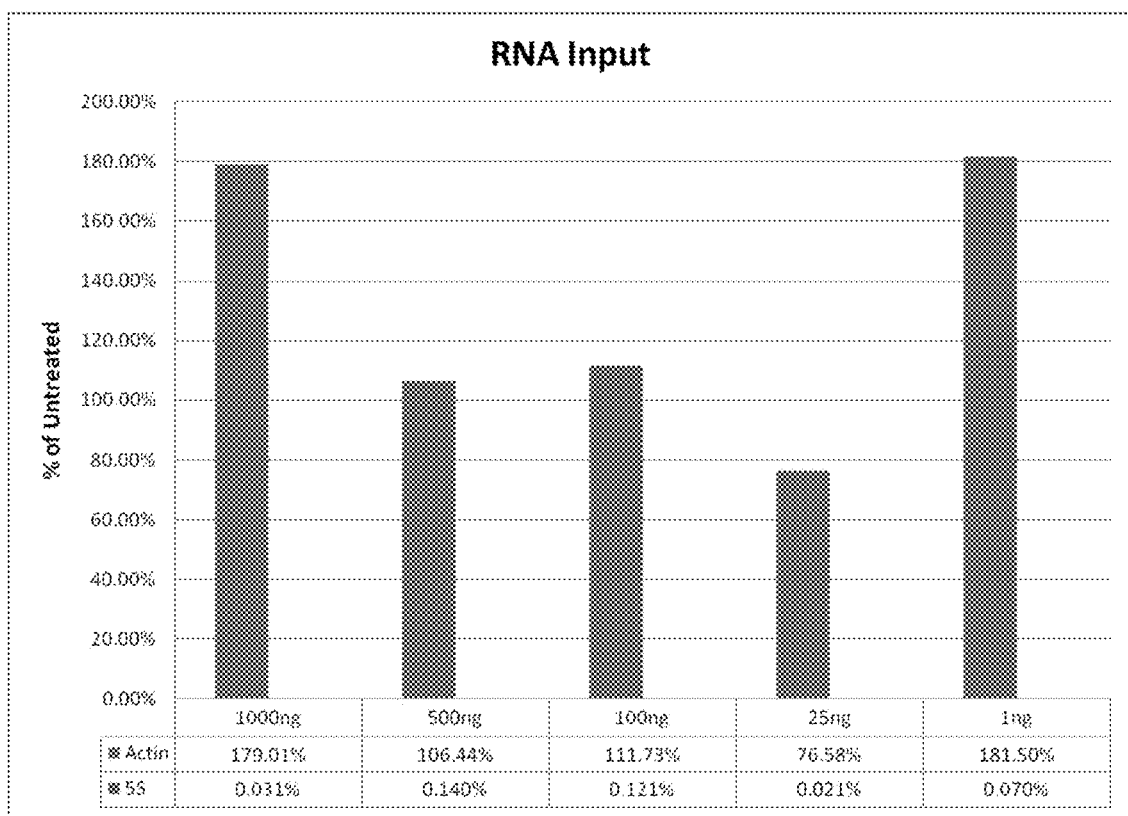
FIG. 5 shows the graphical results from an experiment demonstrating that the targeting primer is capable of selectively depleting 5S transcripts at a range of total RNA amounts, when employed in methods according to an embodiment of the invention.

Total mouse RNA at various amounts (1000 ng, 500 ng, 100 ng, 25 ng, and 1 ng) was annealed to three, thirty nucleotide primers at a concentration of 2.5 µM each which hybridized along the length of the 5S transcript. The results are shown in FIG. 5. All concentrations of RNA had a treated (with primer) and an untreated sample (without primer). All samples were treated with RNase H, and the remaining RNA was purified with SPRI beads, converted to cDNA with random primers, and amplified by qPCR with primers specific for Actin (blue) or 5S (red). All concentrations of RNA are presented as a percentage of the amplification by the same primers in the untreated sample (not shown). Actin was included to represent the effect of the treatment overall mRNA levels.

E. Both SPRI and Streptavidin (SA) Beads Decrease the Concentration of Biotinylated Targeting Primer.

Figure 6:
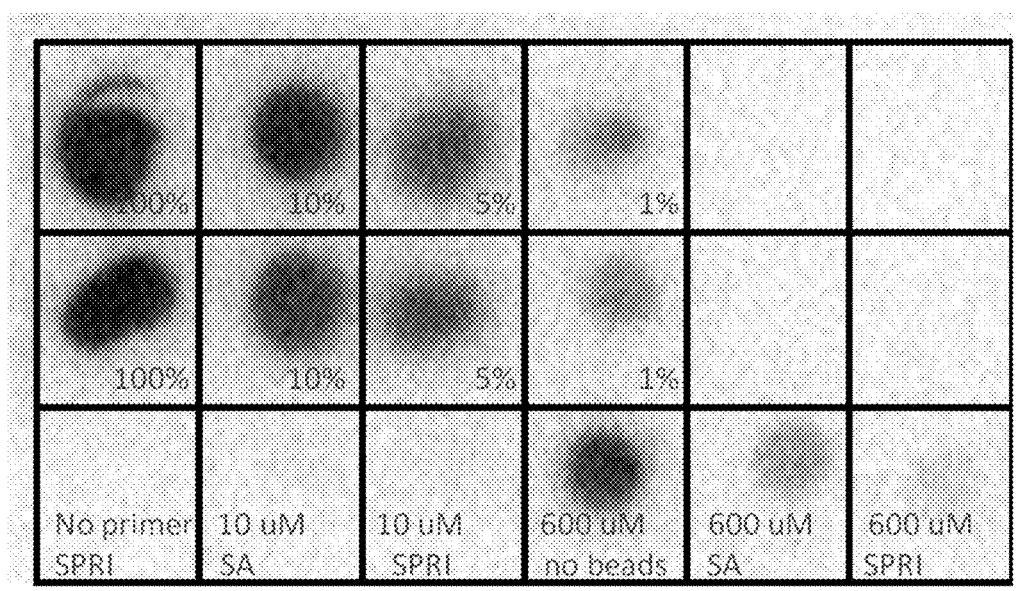
FIG. 6 shows the graphical results from an experiment demonstrating that both SPRI and Streptavidin (SA) beads decrease the concentration of biotinylated targeting primer, when employed in methods according to an embodiment of the invention.

Anti-biotin antibodies were used to visual biotinylated primers cross-linked to a membrane. The results are shown in FIG. 6. A standard curve was created in duplicate (rows 1 and 2) by blotting the equivalent of an entire reaction (100%, 10 µM primers), 10% of a reaction (1 µM), 5% (500 nM), or 1% (100 nM). Samples from experiments are presented on the last row. These experiments either had no primer (far left), 10 µM biotinylated primers (second and third box), or 600 µM (fourth, fifth, and sixth box). RNA was separated from the biotinylated primers with either streptavidin (SA) or SPRI beads and subsequently blotted on the membrane. The fourth box is a 1:30 dilution of an unpurified reaction. The biotinylated primers employed in this experiment are provided in FIG. 7.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A kit comprising:
a polymer cocktail comprising two or more polymers configured to collectively hybridize to less than 80% of a same target nucleic acid, wherein each of the two or more polymers specifically hybridize to distinct regions of the same target nucleic acid to generate hybridized regions of the target nucleic acid that are separated by a gap;
a nuclease capable of specifically cleaving the distinct regions of the target nucleic acid when the two or more polymers are hybridized to the target nucleic acid;
wherein the polymer cocktail is configured to remove the target nucleic acid from a sample comprising the polymer cocktail, the target nucleic acid and the nuclease.

2. The kit according to claim 1, wherein the target nucleic acid is a ribonucleic acid (RNA).

3. The kit according to claim 1, wherein the target nucleic acid is a deoxyribonucleic acid (DNA).

4. The kit according to claim 1, wherein the two or more polymers are independently selected from the group consisting of: a DNA oligonucleotide, an RNA oligonucleotide, a locked nucleic acid (LNA), a peptide nucleic acid (PNA), and a xeno nucleic acid (XNA).

5. The kit according to claim 1, wherein the kit further comprises a component for removing the two or more polymers from a reaction mixture.

6. The kit according to claim 5, wherein the component for removing the two or more polymers from a reaction mixture is an enzyme.

7. The kit according to claim 6, wherein the two or more polymers comprise deoxyuridine triphosphate (dUTP).

8. The kit according to claim 7, wherein the enzyme is uracil-N-glycosylase (UDG).

9. The kit according to claim 5, wherein the component for removing the two or more polymers is a solid support to which the two or more polymers bind.

10. The kit according to claim 1, wherein the nuclease is a ribonuclease.

11. The kit according to claim 10, wherein the ribonuclease is selected from the group consisting of RNase H and RNase V.

12. The kit according to claim 1, wherein the nuclease is a deoxyribonuclease.

13. The kit according to claim 1, comprising a buffer compatible with the nuclease.

14. The kit according to claim 1, comprising reagents for isolating nucleic acids from a nucleic acid source.

15. The kit according to claim 1, wherein the polymer cocktail comprises 3 or more polymers.

16. The kit according to claim 1, wherein the polymer cocktail comprises 4 or more polymers.

17. The kit according to claim 1, wherein the polymer cocktail comprises 2 to 30 polymers.

18. The kit according to claim 1, wherein the two or more polymers are 10 to 200 nucleotides in length.

19. The kit according to claim 1, wherein the two or more polymers are 10 to 50 nucleotides in length.

20. The kit according to claim 1, wherein the polymer cocktail comprises polymers that hybridize to two or more different target nucleic acids.

21. The kit according to claim 1, wherein the two or more polymers are unlabeled.

22. The kit according to claim 2, wherein the ribonucleic acid is selected from the group consisting of: a ribosomal RNA (rRNA), a precursor messenger RNA (pre-mRNA), a micro RNA (miRNA), a transfer RNA (tRNA), a mitochondrial RNA (mtRNA), and any combination thereof.

23. The kit according to claim 22, wherein the ribonucleic acid is a ribosomal ribonucleic acid (rRNA).

* * * * *

UNITED STATES PATENT AND TRADEMARK OFFICE
CERTIFICATE OF CORRECTION

PATENT NO. : 11,149,303 B2  
APPLICATION NO. : 16/537160  
DATED : October 19, 2021  
INVENTOR(S) : Andrew Alan Farmer et al.

Page 1 of 1

It is certified that error appears in the above-identified patent and that said Letters Patent is hereby corrected as shown below:

In the Specification

Please replace "100 nM to 100" with -- 100 nM to 10µM -- (Column 6, Line 9).

Please replace "500 nM to 2.50" with -- 500nM to 2.5µM -- (Column 6, Line 10).

Signed and Sealed this  
Twenty-third Day of November, 2021

Drew Hirshfeld  
*Performing the Functions and Duties of the*  
*Under Secretary of Commerce for Intellectual Property and*  
*Director of the United States Patent and Trademark Office*

SEQUENCE LISTING

```
<160> NUMBER OF SEQ ID NOS: 189

<210> SEQ ID NO 1
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 1
ggtattccca ggcggtctcc catccaagta                                        30

<210> SEQ ID NO 2
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 2
cacgagccga gtgatccacc gctaagagtc                                        30

<210> SEQ ID NO 3
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 3
tcacattaat tctcgcagct agctgcgttc                                        30
```

```
<210> SEQ ID NO 4
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 4
aagtgcgttc gaagtgtcga tgatcaatgt                                        30

<210> SEQ ID NO 5
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 5
gttcctcccg gggctacgcc tgtctgagcg                                        30

<210> SEQ ID NO 6
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 6
gcatatgcta ctggcaggat caaccaggta                                        30

<210> SEQ ID NO 7
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 7
cgtgcgtact cagacatgca tggcttaatc                                        30

<210> SEQ ID NO 8
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 8
aactgattta atgagccatt cgcagtttca                                        30

<210> SEQ ID NO 9
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 9
ttatccaagt aggagaggag cgagcgacca                                        30

<210> SEQ ID NO 10
<211> LENGTH: 29
<212> TYPE: DNA
<213> ORGANISM: Artificial Sequence
<220> FEATURE:
<223> OTHER INFORMATION: Synthetic Nucleic Acid Sequence
```

```
<400> SEQUENCE: 10
cagcgcccgt cggcatgtat tagctctag                                        29

<210> SEQ ID NO 11
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 11
ttgatctgat aaatgcacgc atcccccccg                                       30

<210> SEQ ID NO 12
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 12
gccggggccg gagaggggct gaccgggttg                                       30

<210> SEQ ID NO 13
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 13
gcccgaggtt atctagagtc accaaagccg                                       30

<210> SEQ ID NO 14
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 14
gttcgaatgg gtcgtcgccg ccacgggggg                                       30

<210> SEQ ID NO 15
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 15
gtaggcacgg cgactaccat cgaaagttga                                       30

<210> SEQ ID NO 16
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 16
ggaatcgaac cctgattccc cgtcacccgt                                       30

<210> SEQ ID NO 17
<211> LENGTH: 30
```

```
<212> TYPE: DNA
<213> ORGANISM: Artificial Sequence
<220> FEATURE:
<223> OTHER INFORMATION: Synthetic Nucleic Acid Sequence

<400> SEQUENCE: 17
cttccttgga tgtggtagcc gtttctcagg                                        30

<210> SEQ ID NO 18
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 18
cctccccggg tcgggagtgg gtaatttgcg                                        30

<210> SEQ ID NO 19
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 19
gggcctcgaa agagtcctgt attgttattt                                        30

<210> SEQ ID NO 20
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 20
tcctcgttaa aggatttaaa gtggactcat                                        30

<210> SEQ ID NO 21
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 21
agctggaatt accgcggctg ctggcaccag                                        30

<210> SEQ ID NO 22
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 22
tttaactgca gcaactttaa tatacgctat                                        30

<210> SEQ ID NO 23
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 23
```
gcggaccgcc cgcccgctcc caagatccaa                                              30

<210> SEQ ID NO 24
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 24
gagaggcaag gggcggggac gggcggtggc                                              30

<210> SEQ ID NO 25
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 25
gccccgcggg acactcagct aagagcatcg                                              30

<210> SEQ ID NO 26
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 26
tgctttgaac actctaattt tttcaaagta                                              30

<210> SEQ ID NO 27
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 27
ttccattatt cctagctgcg gtatccaggc                                              30

<210> SEQ ID NO 28
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 28
cctcagttcc gaaaaccaac aaaatagaac                                              30

<210> SEQ ID NO 29
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 29
gcgcaatacg aatgccccg gccgtccctc                                               30

<210> SEQ ID NO 30
<211> LENGTH: 30
<212> TYPE: DNA
<213> ORGANISM: Artificial Sequence

```
<220> FEATURE:
<223> OTHER INFORMATION: Synthetic Nucleic Acid Sequence

<400> SEQUENCE: 30
tggtccgtct tgcgccggtc caagaatttc                                              30

<210> SEQ ID NO 31
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 31
taatgaaaac attcttggca aatgctttcg                                              30

<210> SEQ ID NO 32
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 32
tacgacggta tctgatcgtc ttcgaacctc                                              30

<210> SEQ ID NO 33
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 33
tacgacggta tctgatcgtc ttcgaacctc                                              30

<210> SEQ ID NO 34
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 34
cgccgccgca tcgccggtcg gcatcgttta                                              30

<210> SEQ ID NO 35
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 35
tttgcaacca tactcccccc ggaacccaaa                                              30

<210> SEQ ID NO 36
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 36
gctccactcc tggtggtgcc cttccgtcaa                                              30
```

<210> SEQ ID NO 37
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 37
ccgggtgagg tttcccgtgt tgagtcaaat                              30

<210> SEQ ID NO 38
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 38
agaaagagct atcaatctgt caatcctgtc                              30

<210> SEQ ID NO 39
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 39
accaactaag aacggccatg caccaccacc                              30

<210> SEQ ID NO 40
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 40
agtctcgttc gttatcggaa ttaaccagac                              30

<210> SEQ ID NO 41
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 41
gccgaccgct cggggtcgc gtaactagtt                              30

<210> SEQ ID NO 42
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 42
gtggctgaac gccacttgtc cctctaagaa                              30

<210> SEQ ID NO 43
<211> LENGTH: 30
<212> TYPE: DNA
<213> ORGANISM: Artificial Sequence
<220> FEATURE:
<223> OTHER INFORMATION: Synthetic Nucleic Acid Sequence -continued

<400> SEQUENCE: 43
catctaaggg catcacagac ctgttattgc                            30

<210> SEQ ID NO 44
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 44
cacgctgagc cagtcagtgt agcgcgcgtg                            30

<210> SEQ ID NO 45
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 45
gttcaacggg ttacccgcgc ctgccggcgt                            30

<210> SEQ ID NO 46
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 46
tggggaataa ttgcaatccc cgatccccat                            30

<210> SEQ ID NO 47
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 47
gcaagcttat gacccgcact tactgggaat                            30

<210> SEQ ID NO 48
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 48
gcgacgggcg gtgtgtacaa agggcaggga                            30

<210> SEQ ID NO 49
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 49
gccgatccga gggcctcact aaaccatcca                            30

<210> SEQ ID NO 50

```
<210> SEQ ID NO 50
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 50
tctcagcgct ccgccagggc cgtgggccga                                      30

<210> SEQ ID NO 51
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 51
ccttgttacg acttttactt cctctagata                                      30

<210> SEQ ID NO 52
<211> LENGTH: 29
<212> TYPE: DNA
<213> ORGANISM: Artificial Sequence
<220> FEATURE:
<223> OTHER INFORMATION: Synthetic Nucleic Acid Sequence

<400> SEQUENCE: 52
taatgatcct tccgcaggtt cacctacgg                                       29

<210> SEQ ID NO 53
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 53
gcgggtcgcc acgtctgatc tgaggtcgcg                                      30

<210> SEQ ID NO 54
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 54
ttagtttctt ctcctccgct gactaatatg                                      30

<210> SEQ ID NO 55
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 55
gctcttccct gttcactcgc cgttactgag                                      30

<210> SEQ ID NO 56
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 56
```
gcgccccgcc gcggggcggg gattcggcgc                                              30

<210> SEQ ID NO 57
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 57
cccacgagcg gcgccgggga gcgggtcttc                                              30

<210> SEQ ID NO 58
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 58
ccgtccacgg gctgggcctc gatcagaagg                                              30

<210> SEQ ID NO 59
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 59
cccggcgcgc cggggccgc taccggcctc                                               30

<210> SEQ ID NO 60
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 60
cgctttgggc tgcattccca agcaacccga                                              30

<210> SEQ ID NO 61
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 61
gtctcgtgcc ggtatttagc cttagatgga                                              30

<210> SEQ ID NO 62
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 62
tcaactttcc cttacggtac ttgttgacta                                              30

<210> SEQ ID NO 63
<211> LENGTH: 30
<212> TYPE: DNA

<213> ORGANISM: Artificial Sequence
<220> FEATURE:
<223> OTHER INFORMATION: Synthetic Nucleic Acid Sequence

<400> SEQUENCE: 63
ctcttaacgg tttcacgccc tcttgaactc                            30

<210> SEQ ID NO 64
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 64
tgaatcctcc gggcggactg cgcggacccc                            30

<210> SEQ ID NO 65
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 65
gggccgccga cacggccgga cccgccgccg                            30

<210> SEQ ID NO 66
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 66
gggcgggtgg aggggtcggg aggaacgggg                            30

<210> SEQ ID NO 67
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 67
agcccgcccc ctccggggag gaggaggagg                            30

<210> SEQ ID NO 68
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 68
ccggccccgc ccgcccaccc ccgcacccgc                            30

<210> SEQ ID NO 69
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 69
cggtcgccgg tcgggggacg gtcccccgcc                            30

<210> SEQ ID NO 70
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 70
cgcggcgcac cgccgcggtg gaaatgcgcc                                    30

<210> SEQ ID NO 71
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 71
accttccccg ccgggccttc ccagccgtcc                                    30

<210> SEQ ID NO 72
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 72
cgggggagga ggaggacgga cggacggacg                                    30

<210> SEQ ID NO 73
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 73
cgccctcccg agggaggacg cggggccggg                                    30

<210> SEQ ID NO 74
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 74
ctcggggggg gtttcggtcc cgccgccgcc                                    30

<210> SEQ ID NO 75
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 75
ccgggattcg gcgagtgctg ctgccggggg                                    30

<210> SEQ ID NO 76
<211> LENGTH: 30
<212> TYPE: DNA
<213> ORGANISM: Artificial Sequence
<220> FEATURE:

<223> OTHER INFORMATION: Synthetic Nucleic Acid Sequence

<400> SEQUENCE: 76
gagagcgcgg cgacgggtct cgctccctcg                30

<210> SEQ ID NO 77
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 77
acccccctcg cggggattc cccgcggggg                30

<210> SEQ ID NO 78
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 78 ccccccacg aggagacgcc ggcgcgcccc                30

<210> SEQ ID NO 79
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 79
ggggtgggag agcggtcgcg ccgtgggagg                30

<210> SEQ ID NO 80
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 80
ccgcgcgcgg caccccccc gtcgccgggg                30

<210> SEQ ID NO 81
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 81
gcgcactggg gacagtccgc cccgccccccc                30

<210> SEQ ID NO 82
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 82
agagaacctc ccccgggccc gacggcgcga                30

<210> SEQ ID NO 83
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 83
tccgccgtcc ccctcttcgg gggacgcgcg                                       30

<210> SEQ ID NO 84
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 84
ggggtcggcg gcgacgtcgg ctacccaccc                                       30

<210> SEQ ID NO 85
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 85
gcacgtgtta gactccttgg tccgtgtttc                                       30

<210> SEQ ID NO 86
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 86
cattgcgcca cggcggcttt cgtgcgagcc                                       30

<210> SEQ ID NO 87
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 87
ggatcccacc tcggccggcg agcgcgccgg                                       30

<210> SEQ ID NO 88
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 88
gtggtgcgcc ctcggcggac tggagaggcc                                       30

<210> SEQ ID NO 89
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 89
cgtgcgctcg tgctccacct ccccggcgcg                                30

<210> SEQ ID NO 90
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 90
ccctgcccag gcatagttca ccatctttcg                                30

<210> SEQ ID NO 91
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 91
ggaccgctac ggacctccac cagagttttcc                               30

<210> SEQ ID NO 92
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 92
tcgcccctat acccaggtcg gacgaccgat                                30

<210> SEQ ID NO 93
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 93
cttcggaggg aaccagctac tagatggttc                                30

<210> SEQ ID NO 94
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 94
gatagctggc gctctcgcag acccgacgca                                30

<210> SEQ ID NO 95
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 95
ctaatcattc gctttaccgg ataaaactgc                                30

<210> SEQ ID NO 96
<211> LENGTH: 30

```
<212> TYPE: DNA
<213> ORGANISM: Artificial Sequence
<220> FEATURE:
<223> OTHER INFORMATION: Synthetic Nucleic Acid Sequence

<400> SEQUENCE: 96
gccgaaacga tctcaaccta ttctcaaact                                    30

<210> SEQ ID NO 97
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 97
ccggctccac gccagcgagc cgggcttctt                                    30

<210> SEQ ID NO 98
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 98
gcttaccaaa agtggcccac taggcactcg                                    30

<210> SEQ ID NO 99
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 99
ccttaacccg gcgttcggtt catcccgcag                                    30

<210> SEQ ID NO 100
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 100
aacacctttt ctggggtctg atgagcgtcg                                    30

<210> SEQ ID NO 101
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 101
tccgacttcc atggccaccg tcctgctgtc                                    30

<210> SEQ ID NO 102
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 102
```
ttgattcggc aggtgagttg ttacacactc        30

<210> SEQ ID NO 103
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 103
cgacgctcca gcgccatcca ttttcagggc        30

<210> SEQ ID NO 104
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 104
gccgctcccg tccactctcg actgccggcg        30

<210> SEQ ID NO 105
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 105
tccgacgcac accacacgcg cgcgcgcgcg        30

<210> SEQ ID NO 106
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 106
gaaggacccc acaccccgc cgccgccgcc         30

<210> SEQ ID NO 107
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 107
aggaggggag gaggcgtggg ggggggggcg        30

<210> SEQ ID NO 108
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 108
cgtagcgtcc gcggggctcc ggggggcgggg       30

<210> SEQ ID NO 109
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 109
gcttcaaggc tcaccgcagc ggccctccta                             30

<210> SEQ ID NO 110
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 110
cctgcggcgg ctccacccgg gcccgcgccc                             30

<210> SEQ ID NO 111
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 111
cttcaaagtt ctcgtttgaa tatttgctac                             30

<210> SEQ ID NO 112
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 112
gttcaactgc tgttcacatg gaacccttct                             30

<210> SEQ ID NO 113
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 113
ggaacggcgc tcgcccatct ctcaggaccg                             30

<210> SEQ ID NO 114
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 114
cgatcggccg agggcaacgg aggccatcgc                             30

<210> SEQ ID NO 115
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 115
ccgccactcc ggattcgggg atctgaaccc                             30

<210> SEQ ID NO 116
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 116
gttaccgcac tggacgcctc gcggcgccca					30

<210> SEQ ID NO 117
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 117
tctccccggg gctcccgccg gcttctccgg					30

<210> SEQ ID NO 118
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 118
ccattccagg gcgccctgcc cttcacaaag					30

<210> SEQ ID NO 119
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 119
ggaaccgcga cgctttccaa ggcacgggcc					30

<210> SEQ ID NO 120
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 120
tctcccccgg attttcaagg gccagcgaga					30

<210> SEQ ID NO 121
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 121
atatgggtac ggcccggcgc gagatttaca					30

<210> SEQ ID NO 122
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 122
caacatgcca gaggctgttc accttggaga                                    30

<210> SEQ ID NO 123
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 123
tacggatccg gcttgccgac ttcccttacc                                    30

<210> SEQ ID NO 124
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 124
cgaccgaccc agcccttaga gccaatcctt                                    30

<210> SEQ ID NO 125
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 125
cgcctcgtcc agccgcggcg cgcgcccagc                                    30

<210> SEQ ID NO 126
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 126
gggggtgccc cgggcgtggg gggggcggcg                                    30

<210> SEQ ID NO 127
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 127
gcgcggggtg gggcggggga gggccgcgag                                    30

<210> SEQ ID NO 128
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 128
ggggagagag agagagagag ggcgcggggc                                    30

<210> SEQ ID NO 129

```
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 129
cacgcggcgc tcccccgggg aggggggagg                                        30

<210> SEQ ID NO 130
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 130
gcccctgccg ccccgaccct tctcccccg                                         30

<210> SEQ ID NO 131
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 131
cgccggcccc ccgggtgccc gggccccct                                         30

<210> SEQ ID NO 132
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 132
aagggcccgg ctcgcgtcca gagtcgccgc                                        30

<210> SEQ ID NO 133
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 133
ccgggctccc cggggggcggc cgcgacgccc                                       30

<210> SEQ ID NO 134
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 134
gacgagacgt ggggtggggg gggggcgcg                                         30

<210> SEQ ID NO 135
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 135
```
ccgccgcccg accgctcccc gcccccagcg                                          30

<210> SEQ ID NO 136
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 136
ggggtagggc gggggacga accgccccgc                                           30

<210> SEQ ID NO 137
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 137
aggaggaggg gggaacgggg ggcggacggg                                          30

<210> SEQ ID NO 138
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 138
gccgcgcgcc gaggaggagg ggggaacggg                                          30

<210> SEQ ID NO 139
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 139
ggcggacccg gcggggggga ccggcccgcg                                          30

<210> SEQ ID NO 140
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 140
ccggccgagg cgaggcgccg cgcggaaccg                                          30

<210> SEQ ID NO 141
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 141
ttcccctggt ccgcaccagt tctaagtcgg                                          30

<210> SEQ ID NO 142
<211> LENGTH: 30
<212> TYPE: DNA

<213> ORGANISM: Artificial Sequence
<220> FEATURE:
<223> OTHER INFORMATION: Synthetic Nucleic Acid Sequence

<400> SEQUENCE: 142
gcgggccttc gcgatgcttt gttttaatta                              30

<210> SEQ ID NO 143
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 143
ctgggcagaa atcacatcgc gtcaacaccc                              30

<210> SEQ ID NO 144
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 144
cgtttacccg cgcttcattg aatttcttca                              30

<210> SEQ ID NO 145
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 145
tggctacctt aagagagtca tagttactcc                              30

<210> SEQ ID NO 146
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 146
tctcgttcat ccattcatgc gcgtcactaa                              30

<210> SEQ ID NO 147
<211> LENGTH: 31
<212> TYPE: DNA
<213> ORGANISM: Artificial Sequence
<220> FEATURE:
<223> OTHER INFORMATION: Synthetic Nucleic Acid Sequence

<400> SEQUENCE: 147
ggctgtggtt tcgctggata gtaggtaggg a                            31

<210> SEQ ID NO 148
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 148
ggtcttcttt ccccgctgat tccgccaagc                              30

<210> SEQ ID NO 149
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 149
atgtctcttc accgtgccag actagagtca                                    30

<210> SEQ ID NO 150
<211> LENGTH: 31
<212> TYPE: DNA
<213> ORGANISM: Artificial Sequence
<220> FEATURE:
<223> OTHER INFORMATION: Synthetic Nucleic Acid Sequence

<400> SEQUENCE: 150 ggggggggcgc cggggggcctc ccacttattc t                                31

<210> SEQ ID NO 151
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 151
cggaccccgc cccgggcccc tcgcggggac                                    30

<210> SEQ ID NO 152
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 152
aaaaacgatc agagtagtgg tatttcaccg                                    30

<210> SEQ ID NO 153
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 153
gggctcgccc ccccgcctca ccgggtcagt                                    30

<210> SEQ ID NO 154
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 154
cgcgcggccg ggcgcttggc gccagaagcg                                    30

<210> SEQ ID NO 155
<211> LENGTH: 30
<212> TYPE: DNA
<213> ORGANISM: Artificial Sequence
<220> FEATURE:

<223> OTHER INFORMATION: Synthetic Nucleic Acid Sequence

<400> SEQUENCE: 155
aaactcccca cctggcactg tccccggagc                30

<210> SEQ ID NO 156
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 156
gacacctgcg ttaccgtttg acaggtgtac                30

<210> SEQ ID NO 157
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 157
gctccacggg aggtttctgt cctccctgag                30

<210> SEQ ID NO 158
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 158
tcgtactgaa aatcaagatc aagcgagctt                30

<210> SEQ ID NO 159
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 159
ggtcagaagg atcgtgaggc cccgctttca                30

<210> SEQ ID NO 160
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 160
tgtggtaact tttctgacac ctcctgctta                30

<210> SEQ ID NO 161
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 161
cgtcgctatg aacgcttggc cgccacaagc                30

```
<210> SEQ ID NO 162
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 162
caatgatagg aagagccgac atcgaaggat                                      30

<210> SEQ ID NO 163
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 163
tagtgggtga acaatccaac gcttggtgaa                                      30

<210> SEQ ID NO 164
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 164
cctgtctcac gacggtctaa acccagctca                                      30

<210> SEQ ID NO 165
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 165
ggcaacaaca catcatcagt agggtaaaac                                      30

<210> SEQ ID NO 166
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 166
caaatgtctg aacctgcggt tcctctcgta                                      30

<210> SEQ ID NO 167
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 167
gtagcttcgc cccattggct cctcagccaa                                      30

<210> SEQ ID NO 168
<211> LENGTH: 30
<212> TYPE: DNA
<213> ORGANISM: Artificial Sequence
<220> FEATURE:
<223> OTHER INFORMATION: Synthetic Nucleic Acid Sequence
```

<400> SEQUENCE: 168
gattctgact tagaggcgtt cagtcataat                                30

<210> SEQ ID NO 169
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 169
cgaggctccg cggcgctgcc gtatcgttcc                                30

<210> SEQ ID NO 170
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 170
ccggcgggga caggcggggg accggctatc                                30

<210> SEQ ID NO 171
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 171
tcccgcgcgc gcggggcgcg tggaggggg                                 30

<210> SEQ ID NO 172
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 172
caccggaccc cggtcccggc gcgcggcggg                                30

<210> SEQ ID NO 173
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 173
ctccggccgc gccccgtttc ccaggacgaa                                30

<210> SEQ ID NO 174
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 174
acgaacgtgc ggtgcgtgac gggcgagggg                                30

<210> SEQ ID NO 175
<211> LENGTH: 30

<212> TYPE: DNA
<213> ORGANISM: Artificial Sequence
<220> FEATURE:
<223> OTHER INFORMATION: Synthetic Nucleic Acid Sequence

<400> SEQUENCE: 175
gaagcaggtc gtctacgaat ggtttagcgc                                    30

<210> SEQ ID NO 176
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 176
agcgagggag ctgctctgct acgtacgaaa                                    30

<210> SEQ ID NO 177
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 177
gacaaaccct tgtgtcgagg gctgactttc                                    30

<210> SEQ ID NO 178
<211> LENGTH: 59
<212> TYPE: DNA
<213> ORGANISM: Artificial Sequence
<220> FEATURE:
<223> OTHER INFORMATION: Synthetic Nucleic Acid Sequence

<400> SEQUENCE: 178
aagtactaac caggcccgac cctgcttagc ttccgaggtc atagctgttt cctgtgtga    59

<210> SEQ ID NO 179
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 179
aagcctacag cacccggtat tcccaggcgg                                    30

<210> SEQ ID NO 180
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 180
aagtactaac caggcccgac cctgcttagc                                    30

<210> SEQ ID NO 181
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 181
agacgagatc gggcgcgttc agggtggtat                                                    30

<210> SEQ ID NO 182
<211> LENGTH: 20
<212> TYPE: DNA
<213> ORGANISM: Artificial Sequence
<220> FEATURE:
<223> OTHER INFORMATION: Synthetic Nucleic Acid Sequence

<400> SEQUENCE: 182
aagcctacag cacccggtat                                                               20

<210> SEQ ID NO 183
<211> LENGTH: 20
<212> TYPE: DNA
<213> ORGANISM: Artificial Sequence
<220> FEATURE:
<223> OTHER INFORMATION: Synthetic Nucleic Acid Sequence

<400> SEQUENCE: 183
tctcccatcc aagtactaac                                                               20

<210> SEQ ID NO 184
<211> LENGTH: 20
<212> TYPE: DNA
<213> ORGANISM: Artificial Sequence
<220> FEATURE:
<223> OTHER INFORMATION: Synthetic Nucleic Acid Sequence

<400> SEQUENCE: 184
cctgcttagc ttccgagatc                                                               20

<210> SEQ ID NO 185
<211> LENGTH: 20
<212> TYPE: DNA
<213> ORGANISM: Artificial Sequence
<220> FEATURE:
<223> OTHER INFORMATION: Synthetic Nucleic Acid Sequence

<400> SEQUENCE: 185
gggcgcgttc agggtggtat                                                               20

<210> SEQ ID NO 186
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 186
cacgagccga gtgatccacc gctaagagtc                                                    30

<210> SEQ ID NO 187
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 187
tcacattaat tctcgcagct agctgcgttc                                                    30

<210> SEQ ID NO 188
<211> LENGTH: 30
<212> TYPE: DNA
<213> ORGANISM: Artificial Sequence

```
<220> FEATURE:
<223> OTHER INFORMATION: Synthetic Nucleic Acid Sequence

<400> SEQUENCE: 188
aagtgcgttc gaagtgtcga tgatcaatgt                                    30

<210> SEQ ID NO 189
<211> LENGTH: 30
<212> TYPE: DNA
<213> ORGANISM: Artificial Sequence
<220> FEATURE:
<223> OTHER INFORMATION: Synthetic Nucleic Acid Sequence

<400> SEQUENCE: 189
gttcctcccg gggctacgcc tgtctgagcg                                    30
```